US011186867B2

(12) United States Patent
Daum et al.

(10) Patent No.: US 11,186,867 B2
(45) Date of Patent: Nov. 30, 2021

(54) NEXT GENERATION GENOMIC SEQUENCING METHODS

(71) Applicant: Longhorn Vaccines and Diagnostics, LLC, Bethesda, MD (US)

(72) Inventors: Luke T. Daum, San Antonio, TX (US); Gerald W. Fischer, Bethesda, MD (US)

(73) Assignee: Longhorn Vaccines and Diagnostics, LLC, Bethesda, MD (US)

( * ) Notice: Subject to any disclaimer, the term of this patent is extended or adjusted under 35 U.S.C. 154(b) by 0 days.

(21) Appl. No.: 15/448,966

(22) Filed: Mar. 3, 2017

(65) Prior Publication Data

US 2017/0183725 A1 Jun. 29, 2017

Related U.S. Application Data

(63) Continuation of application No. 14/527,281, filed on Oct. 29, 2014, now Pat. No. 9,598,737, which is a continuation of application No. 13/890,512, filed on May 9, 2013, now Pat. No. 9,365,904.

(60) Provisional application No. 61/897,015, filed on Oct. 29, 2013, provisional application No. 61/737,250, filed on Dec. 14, 2012, provisional application No. 61/695,960, filed on Aug. 31, 2012, provisional application No. 61/646,060, filed on May 11, 2012, provisional application No. 61/644,876, filed on May 9, 2012.

(51) Int. Cl.
*C12Q 1/68* (2018.01)
*C12Q 1/6869* (2018.01)
*C12Q 1/689* (2018.01)
*C12Q 1/70* (2006.01)

(52) U.S. Cl.
CPC ........... *C12Q 1/6869* (2013.01); *C12Q 1/689* (2013.01); *C12Q 1/701* (2013.01); *C12Q 2600/156* (2013.01); *C12Q 2600/16* (2013.01); *Y02A 50/30* (2018.01)

(58) Field of Classification Search
CPC ............ C12Q 1/6869; C12Q 2563/113; C12Q 2563/116; C12Q 1/689; C12Q 1/701; C12Q 2600/156; C12Q 2600/16; Y02A 50/52; Y02A 50/58
USPC ........................................................ 435/91.2
See application file for complete search history.

(56) References Cited

U.S. PATENT DOCUMENTS

| | | |
|---|---|---|
| 5,550,040 A | 8/1996 | Purohit et al. |
| 6,124,098 A | 9/2000 | Heym et al. |
| 2009/0233292 A1 | 9/2009 | Podini et al. |
| 2009/0305252 A1 | 12/2009 | Li .......................... C12Q 1/689 |
| | | 435/6.15 |
| 2010/0035232 A1* | 2/2010 | Ecker ................... C12Q 1/6806 |
| | | 435/5 |
| 2010/0285479 A1 | 11/2010 | Jenison |
| 2011/0136104 A1* | 6/2011 | Pregibon .............. C12Q 1/6851 |
| | | 435/6.12 |
| 2011/0207135 A1 | 8/2011 | Faham ................. C12Q 1/6883 |
| | | 435/6.11 |
| 2011/0281754 A1 | 11/2011 | Fischer et al. |
| 2011/0281776 A1* | 11/2011 | Eshoo .............. B01L 3/502753 |
| | | 506/40 |
| 2011/0312723 A1* | 12/2011 | Silverbrook .......... B01L 3/5027 |
| | | 506/39 |
| 2012/0034685 A1 | 2/2012 | Sparks et al. |
| 2012/0037531 A1 | 3/2012 | Pollner et al. |
| 2012/0100549 A1* | 4/2012 | Eshoo .................... C12Q 1/686 |
| | | 435/6.12 |
| 2012/0129794 A1 | 5/2012 | Dowd .................. C12Q 1/6809 |
| | | 514/24 |
| 2012/0295819 A1 | 11/2012 | Leamon et al. |
| 2013/0302789 A1 | 11/2013 | Daum et al. |
| 2015/0184231 A1 | 7/2015 | Ecker ................... C12Q 1/6853 |
| | | 506/7 |

FOREIGN PATENT DOCUMENTS

| | | |
|---|---|---|
| CN | 102 250 924 A | 11/2011 |
| CN | 102250924 | 11/2011 |

(Continued)

OTHER PUBLICATIONS

CN Exam Report for Application No. 2013 80024174.5 dated Jan. 4, 2018.

(Continued)

*Primary Examiner* — Cynthia B Wilder
(74) *Attorney, Agent, or Firm* — Remenick PLLC

(57) ABSTRACT

Disclosed is an enhanced method for rapid and cost-effective analysis of sequences of a microorganism by semi-conductor sequencing, preferably ion-torrent sequencing. This method provides for full length analysis and of multiple areas (e.g. genes) of multiple genomes. These methods identify genetic mutations of a particular gene that are responsible for conferring resistance or sensitivity to an antibiotic or other chemical compound. Multiple different species, strains and/or serotypes of a particular organism are rapidly and efficiently screened and mutations identified along with the complete genome of an organism. By selecting primers pairs of similar size and GC content that produce amplicons with sequences spanning the entire genome, a single PCR reaction analyzed by ion torrent methodology can determine the sequence of a complete genome. Methods are useful to sequences the genomes of viral agents, such as influenza virus, and bacterial agents, such as *tuberculosis* bacteria.

25 Claims, 18 Drawing Sheets

Specification includes a Sequence Listing.

(56) References Cited

FOREIGN PATENT DOCUMENTS

| WO | WO 03/080870 | 10/2003 |
|---|---|---|
| WO | WO2003/080870 | 10/2003 |
| WO | WO2005/001128 | 1/2005 |
| WO | WO 2005/001128 | 1/2005 |
| WO | WO2006/110855 | 10/2006 |
| WO | WO 2012/037531 | 3/2012 |
| WO | WO2012/037531 | 3/2012 |
| WO | WO 2012/149438 | 11/2012 |
| WO | WO 03/080870 | 10/2013 |

OTHER PUBLICATIONS

CN Exam Report for Application No. 2013 80024174.5 dated Jan. 4, 2018 (translation).
CA Examination Report for Application No. 2,976,934 dated Jun. 21, 2018.
CN Exam Report for Application No. 2013 80024174.5 dated Jul. 31, 2017.
CN Exam Report for Application No. 2013 80024174.5 dated Jul. 31, 2017 (translation).
EPO Exam Report for Application No. 13787564.7 dated Mar. 21, 2017.
AU Exam Report for Application No. 201434214, dated Apr. 5, 2017.
Daum et al, "Genetic analysis of *Mycobacterium tuberculosis* drug-resistance genes from samples shipped in PrimerStore MTM and sequenced using the Next-generation Ion Torrent", (May 4, 2012), p. 1, URL: http://www.lhnvd.com/000_vig_user_files/site_uploaded/54713/ESPIDMTBIonTorrentPoster2012.pdf.
Alexander Mellmann et al, "Prospective Genomic Characterization of the German Enterohemorrhagic *Escherichia coli* O104:H4 Outbreak by Rapid Next Generation Sequencing Technology", PLOS ONE, (Jul. 20, 2011), vol. 6, No. 7.
Howden et al., "Evolution of Multidrug Resistance during *Staphylococcus aureus* Infection Involves Mutation of the Essential Two Component Regulator WaIKR", PLOS Pathogens, (Nov. 10, 2011), vol. 7, No. 11, pp. 1-15.
Chinese Office Action for PCT/US2013/040302, dated Aug. 25, 2015.
Ross et al., Am. J. Clin. Pathol. vol. 136, pp. 527-539, Oct. 2011.
EP Search report for PCT/US2013/040302, dated Jul. 13, 2015.
Daum, et al., "Genetic analysis of *Mycobacterium tuberculosis* drug-resistance genes from samples shipped in PrimerStore MTM and sequenced using the next-generation Ion Torrent," p. 1, www.lhnvd.com, retrieved on Jul. 1, 2015.
Mellmann, et al, "Prospective genomic characterization of the German enterohemorrhagic *Escherichia coli* O104:H4 outbreak by rapid next generation sequencing technology," PLOS ONE, vol. 6, No. 7, Jul. 20, 2011.
Jun-Ichiro Sekiguchi, et al, "Detection of 1-3, 6, 10 multidrug resistance in *Mycobacterium tuberculosis*," Journal of Clinical Microbiology, American Society for Microbiology, vol. 45, No. 1, Jan. 1, 2007.
EP Search and Examination Report for Application No. 18182794.0 dated Jan. 16, 2019.
L.T. Daum et al., "Genetic Analysis of *Mycobacterium tuberculosis* drug-resistance genes from samples shipped in PrimerStore MTM and sequenced using the Next-generation Ion Torrent," May 4, 2012. (http://www.lhnvd.com/000_vig_user_filed/sire_uploaded/54713/ESPIDNTBionTorentPoster2012.pdf).
Alexander Mellmann et al., "prospective Genomic Characterization of the German Enterohemorrhagic *Escherichia coli* O104:H4 Outbreak by Rapid Next Generation Sequencing Technology," PLOS ONE vol. 6(7):e22751, Jul. 20, 2011.
Jun-Ichiro Sekiguchi et al., "Detection of Multidrug Resistance in *Mycobacterium tuberculosis*," Journal of Microbiology vol. 45(1):179-192 Jan. 1, 2007.
Grabensteiner et al., "Development of a Multiplex RT-PCR for the Simultaneous Detection of Three Viruses of the Honeybee (*Apis mellifera* L.): Acute Bee Paralysis Virus, Black Queen Cell Virus and Sacbrood Virus," Journal of Invertebrate Pathology, vol. 94(3):222-225, Feb. 14, 2007.
L.T. Daum et al., "Next-Generation Ion Torrent Sequencing of Drug Resistance Mutations in *Mycobacterium tuberculosis* Strains," Journal of Clinical Microbiology vol. 50(12):3831-3837, Dec. 1, 2012.
AU Examination Report for Application No. 2017203556 dated Sep. 5, 2018.
CN Examination Report for CN Application No. 201480071698.4 dated Jan. 16, 2019 (translated).
CN Examination Report for CN Application No. 201480071698.4 dated Jan. 16, 2019 (not translated).
CN Search Report for CN Application No. 201480071698.4 dated Jan. 16, 2019 (not translated).
EP Search and Examination Report for Application No. 14856946.0 dated Oct. 16, 2018.
EP Search and Examination Report for Application No. 18182794.0 dated Oct. 4, 2018.
L.T. Daum et al., "Genetic Analysis of *Mycobacterium tuberculosis* drug resistance genes from samples shipped in PrimeStore MTM and sequenced using the Next Generation Ion Torrent," http://lhnvd.com/000_vig_user_files/site_uploaded/54713/ESPIDMTBIonTorrentPoster2012.pdf May 4, 2012.
Alexander Mellmann et al., "Prospective Genomic Characterization of the German Enterohemorrhagic *Eschericia coli* O104:H4 Outbreak by Rapid Next Generation Sequencing Technology," PLOS ONE vol. 6, No. 7, p. e22751, Jul. 20, 2011.
Jun-Ichiro Sekiguchi et al., "Detection of Multidrug Resistance in *Mycobacterium tuberculosis*," J. Clin. Microbiol., vol. 45 No 1, pp. 179-192, Jan. 1, 2007.
Grabensteiner et al., "Development of a multiplex RT-PCR for the simultaneous detection of three viruses of the honeybee (*Apis mellifera* L.): Acute bee paralysis virus, Black Queen cell virus and Sacbrood virus," J. Invert. Pathol. vol. 93, No. 3, pp. 222-225, Feb. 14, 2007.
L.T. Daum et al., "Characterization of Multidrug Resistant *Mycobacterium tuberculosis* from immigrants residing in the USA using Ion Torrent full gene sequencing," Epidemiology and Infection, vol. 142, No. 6, pp. 1328-1333, Sep. 27, 2013.
L.T. Daum et al., "Next Generation Ion Torrent Sequencing of Drug Resistant Mutation in Mycobacterium tuberculosis strains," J. Clin. Microbiol., vol. 50, No. 12, pp. 3831-3837, Dec. 1, 2012.
CN Examination Report for CN Application No. 201480071698.4 dated Jul. 18, 2019 (translated).
CN Examination Report for CN Application No. 201480071698.4 dated Jul. 18, 2019 (not translated).
Examination Report for AU Application No. 2017203556 dated May 17, 2019.
CN Examination Report for CN Application No. 201480071698.4 dated Mar. 19, 2020 (translated).
CN Examination Report for CN Application No. 201480071698.4 dated Mar. 19, 2020 (not translated).
CN Examination Report for CN Application No. 201480071698.4 dated Jan. 4, 2021 (translated).
CN Search Report for CN Application No. 201480071698.4 dated Jan. 4, 2021 (translated).
CN Search and Examination Report for CN Application No. 201480071698.4 dated Jan. 4, 2021 (not translated).
EPO Exam Report Application No. 13787564.7, dated Jun. 21, 2016.
AU Exam Report Application No. 2013259495, dated May 12, 2016.
Canada Office Action for PCTUS2013/040302, dated Oct. 5, 2015.
EP Search Report for PCTUS2013/040302, dated Oct. 8, 2015.
Daum, et al., "Characterization of multi-drug resistant *Mycobacterium tuberculosis* from immigrants residing in the USA using Ion Torrent full-gene sequencing," Epidemiology and Infection, vol. 142, No. 06, pp. 1328-1333, Sep. 27, 2013.
Grabensteiner, et al, "Development of a multiplex RT-PCR for the simultaneous detection of three viruses of the honeybee (*Apis

(56) References Cited

OTHER PUBLICATIONS

*mellifera* L.): Acute bee paralysis virus, Black queen cell virus and Sacbrood virus," Journal of Invertebrate Pathology, vol. 94, No. 3, Feb. 14, 2007.
PCT Search and Patentability Report for PCT/US2014/062889, dated Apr. 3, 2015.
Daum, et al., "Next-Generation Ion Torrent Sequencing of Drug Resistance Mutations in *Mycobacterium tuberculosis* Strains," Journal of Clinical Microbiology, vol. 50, No. 12, pp. 3831-3837, Sep. 12, 2012.
U.S. Appl. No. 13/890,512, Daum, et al.
PCT Search and Patentability Report for PCT/US2013/040302, dated Oct. 4, 2013.
Howden, et al., "Evolution of Multidrug Resistance during *Staphylococcus aureus* Infection Involves Mutation of the Essential Two Component Regulator WalKR," PLoS Pathogens, vol. 7, No. 11, e1002359, pp. 1-15, Nov. 10, 2011.

* cited by examiner pncA gene + 100 flanking base pairs (1161 nt)

AGGCGGAATGAACACCGTCACAGCGTCAGTCCATGCGGACTCGAGTTGCCGAGAGACGAGTTGAGAGATACCCGGCCGGCCGATGAAGGTGTGTGAAGCGG
CCGATGCCTCAATGCCCGCCTGCCACCTGCCGCTGCGAGTTGCCCGGCCATCGCCGTTCGACGTCTTTGAGATGGAAGCGCATCCAACGGCTTCACCGGTC
ATCCCGGTTCGGCCGGTGCCATCGCAAACCTCGAAACGATCTGCGCTTGCCGGTCCCAGCGTCCTCAGTTGCCGACTGGCTCAGTCGTCACACCCTTGCCC
TACCGGTTCCGGCCGTCCGGGCGCCACACTTGAGAACACCGCTGCGAGAACTGTGGCCACAACGATCGACTCCAATCGATGACCTGAAATCGACCGGGCCTAC
CGGGTAGCGACCGCTTGGAAGGCTTGGCAGACACCCGTTGCAGAGACTGGTAGTGCTGGCTTCGCCTGGATGGGAAGAGGCCACGCTGCGGAGCAAGCAGCCCCAGGT
GACGTGCCATGCATCACGCCCCATAGCTTCCGGCAGCTTGGGTGCCGATGGCCTCACGGCGGGCAATGACCGGCCACATGTCACGGGGCGGCCATC
CCAACCGGGGCATGATCAACGCGGATCAACTCCCGAGCTGTCCATCGTCTGGAGTGACGAGCGCACAAATCGCCGCAGTTAGCCCCAGGCCGTCGAACTGCGAT
CCCCATACACGCGGAACAGCCCACATCGTCGTC (SEQ ID NO: 14)

REVERSE COMPLEMENT

GACGACGATGTGCGCTGTTCCGCGTGTATGGGCGATTTGTGCGGTCGACTTGGCGGAAGGCGTCGACGCAAGCCGGCTGGCTACCTGTCACGGATCCGTTTCACCGGATTT
GTCGCTGTACATGCGGGCCTGGAACGCGTTGATCATGCCCCGGTTGGAGTCCAACCGTGGCGACATCCCCGCCGGCCAGCCGCCAAAGCCACACGGCAGGGGAGTTTG
CCCACTGCATCGCTGGAGCAGTTCCACACGGCTCGAACAGAGCATCCGTCCGGGGCAGGAAGCATCTCCACGGCTACCTGCGAAGCGCGCAATCGGTGAGGCCTGACAC
TACCAGTCCGGTGCCTCTAGAGGCGCCGGCGGCCGCCAGGGCTGGCATGTGGCCAACAGGTTGCAAGCAGTCCGAAGCTGTTGTCTAGTGAGACTGGGTATTG
CCAAGCCGATCCATGTGCAGCCTGCTGCAGTTCGAAGCCTCCCACGGCGTACGCCGAAGTCTACTCGGGCCGAAGACACCATTCCGGGCCGACCGGGGCGCCAGCAGTCGCG
AAGTTCCGTTCCCCAAGCGGCATGCCCAGGGGGGCATGCCCAGGGTTACGACACGTTCATCGATGCGGGATATCGATTCGACCGGTTCACCGGTCGTCGCGATCCGACGCAGCGACGA
GGTCCCCGGATGGACGCTGGTGACGGCGTTGATTCATCCCGGCT (SEQ ID NO: 15)

PROTEIN SEQUENCE

MRALIIVDVQNDFCEGGSLAVTGGAALARAISDYLARAADYHHVATKDFHIDPGDHFSGTPDYSSWPPHCVSGTPGADFHPSLDTSAIEAVFYKGAYTGAVSGFEGVDENGPLLNWLRQRGVDEVDVGIATDHCVR
QTAEDAVNGLATRVLVDLTAGVSADTTVAALEEMRTASVELVCSS (SEQ ID NO: 16)
Primer Length:
Forward 1 (20 nt): TCATCGACCCTATATCGTC (SEQ ID NO: 17)
Reverse 1 (20 nt): ATGAACTGTTGGCGGCGGTG (SEQ ID NO: 18)
Amplicon Length: 675 nt Forward 2 (20 nt): ACGGATTGTCGCTCACTAC (SEQ ID NO: 19)
Reverse 2 (20 nt): ATCTGGATATCGATCTCCGGC (SEQ ID NO: 20)
Amplicon Length: 959 nt

*FIG. 1*

From H37RV Gene strain

GGGGCATGCCTCTTCATGCCTTGTCGTCGGGGGGCTTGTGGCCTGCTTGCAACGGGCCTCGCCCTTGTTTGTCAGGAGTGTTTGGCTTTTGTTTGGAGAGTTTGATCCTGGCTC
AGGACGAACGCTGGCGGCGTGCTTAACACATGCAAGTCGAACGGAAAGGTCTCTTCGGAGATACTCGAGTGGCGAACGGGTGAGTAACACGTGGGTAACCTGCCCTGCACTTCGGGATAAGCCTGGGA
AACTGGGTCTAATACCGGATAGGACCACGGGATGCATGTCTTGTGGTGGAAAGCGCTTTAGCGGTGTGGGATGAGCCCGCGGCCTATCAGCTTGTTGGTGGGGTGACGGCCTACCAAGGCGACGACGG
GTAGCCGGCCTGAGAGGGTGTCCGGCCACACTGGGACTGAGATACGGCCCAGACTCCTACGGGAGGCAGCAGTGGGGAATATTGCACAATGGGCGCAAGCCTGATGCAGCGACGCCGCGTGGGGGATG
ACGGCCTTCGGGTTGTAAACCTCTTTCACCATCGACGAAGGTCGCAGTTCTCGGAATGTGTTGACTGTGAAATCTGGCATAGTCTGAATCTGGATCCAGCTCCAGGGTCGGAGCT
GTTGTCCGGAATTACTGGGCGTAAGGGTGTTCCGCAGATATCGGAAATGCGCAGATATACGCCCGTTTCTTGGTGATCGGATGCGTTTCCCTTGTGATCGGATCCAGCTCCAGGGTCG
TCCTGGTGTAGCGGTGAAATGCGCAGATATCAGGAGGAACACCGGTGGCGAAGGCGGGTCTCTGGGCAGTAACTGACGCTGAGGAGCGAAAGCGTGGGGAGCGAACAGGATTAGATACCCTGGTAGTC
CACGCCGTAAACGGTGGGTACTAGGTGTGGGTTTCCTTCCTTGGGATCCGTGCCGTAGCTAACGCATTAAGTACCCCGCCTGGGGAGTACGGTCGCAAGGCTAAAACTCAAAGGAATTGACGGGGGCC
CGCACAAGCGGCGGAGCATGTGGATTAATTCGATGCAACGCGAAGAACCTTACCTGGGTTTGACATGCACAGGACGCGTCTAGAGATAGGTCGGCTTCCCTTGTGGCCTGTGTGCATGGCTG
TCGTCAGCTCGTGTCGTGAGATGTTGGGTTAAGTCCCGCAACGAGCGCAACCCTTGTCTCATGTTGCCAGCACTGTAACAGCGTACACAAAGGGCCTGAGGTCAAGCTACAAAG
TGAGTGTAAGCGATACCCGGGGGAGTACGGCCGCAAGGCTAAAACTCAAAGGAATTGACGGGGGCCCGCACAAGCGGCGGAGCATGTGGATTAATTCGATGCAACGCGAAGAACCTTACCTGGGTTTGACATGCACAGG
CAACTCAAGTCATCATGCCCCTTATGTCTGGGATATGCCCGTGCTACAAGTCCAAAGCCCTTGGGGCGGTGGGCCGTCTCGTCATACAGCGCCGGCTGCGCCTCGTATGCCCTTGTAACCACCAGAGTCGGGGACTTGGGA
CTAACCCTGGAGCGGTAGGGCCCTTGAGGTCTGCTCTACGGGAACTCAATCGGTAACCACCAGAGTCGGGATCACCTTCCTTTCTAAGGAGCGAATCGGCAAAAACGGCCAACT
GGGGGGGTTAGCCCGTCCAGGTCCGGAGAGCCCGAGAGCGAAGGGTGCAAGGAACAGCGCAATGGCGCTAAATGCACCGACAAAGTGCGGCCA (SEQ ID NO: 21)

TB 16S ribosomal RNA gene sequencing primers

PAIR 1:

For 16s Ver1: 5'-TGGCCCGTTGTTTGTCAGGAT-3' (SEQ ID NO: 22)

Rev16s Ver1: 5'-TACAGACAAGAACCCCTCACGG-3' (SEQ ID NO: 23)

Expected amplicon size: 1699 bp

PAIR 2:

For 16s Ver2: 5'-TTCTAAATACCTTTGGCTCCCT-3' (SEQ ID NO: 11)

Rev16s Ver2: 5'-TGGCCAACTTTGTTGTCATGCA-3' (SEQ ID NO: 12)

Expected amplicon size: 1680 bp

*FIG. 2* rpoB gene

Conferring sensitivities/resistance to Rifampin

GATCCGGACAGATCGTTCGCCGGCCGAAACCGACAAAATTATCGCGGCGAACGGGCCCGTGGGCACCGCTCCTCTAAGGGCTCTCGTTGGTCGCATGAAGTGCTGGAAGGATGCATCTTGGCAGATT
CCCGCCAGAGCAAAACAGCCGCTAGTCCTAGTCCGAGTCGCCCGCAAAGTTCCTCGAATAACTCCGTACCCGGAGCGCCAAACCGGGTCTCCTTCGCTAAGCTGCGCGAACCACTTGAGGTTCCGGG
ACTCCTTGACGTCCAGACCGATTCGTTCGAGTGGCTGATCGGTTCGCCGCGCTGGCGCGAATCCGCCGCCGAGCGGGGTGATGTCAACCCAGTGGGTGGCCTGGAAGAGGTGCTCTACGAGCTGTCT
CCGATCGAGGACTTCTCCGGGTCGATGTCGTTGTCGTTCTCTGACCCTCGTTTCGACGATGTCAAGGCACCCGTCGACGAGTGCAAAGACAAGGACATGACGTACGCGGCTCCACTGTTCGTCACCG
CCGAGTTCATCAACAACAACACCGGTGAGATCAAGAGTCAGACGGTGTTCATGGGTGACTTCCCGATGATGACCGAGAAGGGCACGTTCATCATCAACGGGACCGAGCGTGTGGTGGTCAGCCAGCT
GGTGCGGTCGCCCGGGGTGTACTTCGACGAGACCATTGACAAGTCCACCGACAAGACGCTGCACAGCGTCAAGGTGATCCCGAGCCGCGGCGCGTGGCTCGAGTTTGACGTCGACAAGCGCGACACC
GTCGGCGTGCGCATCGACCGCAAACGCCGGCAACCGGTCACCGTGCTGCTCAAGGCGCTGGGCTGGACCAGCGAGCAGATTGTCGAGCGGTTCGGGTTCTCCGAGATCATGCGATCGACGCTGGAGA
AGGACAACACCGTCGGCACCGACGAGGCGCTGTTGGACATCTACCGCAAGCTGCGTCCGGGCGAGCCCCCGACCAAAGAGTCAGCGCAGACGCTGTTGGAAAACTTGTTCTTCAAGGAGAAGCGCTA
CGACCTGGCCCGCGTCGGTCGCTATAAGGTCAACAAGAAGCTCGGGCTGCATGTCGGCGAGCCCATCACGTCGTCGACGCTGACCGAAGAAGACGTCGTGGCCACCATCGAATATCTGGTCCGCTTG
CACGAGGGTCAGACCACGATGACCGTTCCGGGCGGCGTCGAGGTGCCGGTGGAAACCGACGACATCGACCACTTCGGCAACCGCCGCCTGCGTACGGTCGGCGAGCTGATCCAAAACCAGATCCGGG
TCGGCATGTCGCGGATGGAGCGGGTGGTCCGGGAGCGGATGACCACCCAGGACGTGGAGGCGATCACACCGCAGACGTTGATCAACATCCGGCCGGTGGTCGCCGCGATCAAGGAGTTCTTCGGCAC
CAGCCAGCTGAGCCAATTCATGGACCAGAACAACCCGCTGTCGGGGTTGACCCACAAGCGCCGACTGTCGGCGCTGGGCCCCGGCGGTCTGTCACGTGAGCGTGCCGGGCTGGAGGTCCGCGACGTG
CACCCGTCGCACTACGGCCGGATGTGCCCGATCGAAACCCCTGAGGGGCCCAACATCGGTCTGATCGGCTCGCTGTCGGTGTACGCGCGGGTCAACCCGTTCGGGTTCATCGAAACGCCGTACCGCA
AGGTGGTCGACGGCGTGGTTAGCGACGAGATCGTGTACCTGACCGCCGACGAGGAGGACCGCCACGTGGTGGCACAGGCCAATTCGCCGATCGATGCGGACGGTCGCTTCGTCGAGCCGCGC
(SEQ ID NO: 24)

TB.rpoB. Forward Primer1: ACCGACAAAATTATCGCGGCGA (SEQ ID NO: 25)

TB.rpoB. Reverse Primer1: ATCGATCGGCGAATTGGCCTGT (SEQ ID NO: 26)

Amplicon length: 1718 bp

TB.rpoB. Forward Primer2: TCCTCTAAGGGCTCTCGTT (SEQ ID NO: 1)

TB.rpoB. Reverse Primer2: GTCAGGTACACGATCTCGT (SEQ ID NO: 2)

Amplicon length: 1704 bp

FIG. 3

(SEQ ID NO: 27) TCGCCGCGATCAAGGAGT = Reverse Primer from Article EID (Emerging Infectious Diseases)- 2001

(SEQ ID NO: 28) TGGAGGTCCGCGACGTGCA = Forward Primer from Article EID - 2001

TCG = codon 531 Serine to Luecine mutation

CAC = codon 526 Hisidine to Asparagine mutation

TCG = codon 522 Serine to Leucine mutation

GAC = codon 516 Aspartic acid to Valine

CAA = codon 513 Glutamine to Lysine

CTG = codon 533 Leucine to Proline

ATC = codon 572 Isoleucine to Phenylalanine

New Forward Primer

TB.rpoB. Forward Primer3: AATATCTGGTCCGCTTGCACGA (SEQ ID NO: 29)

With TB.rpoB.Reverse Primer is 620 bps

FIG. 3
Continue

Mycobacterium tuberculosis H37Ra, complete genome

GenBank: CP000611.1

GyrA Gene

GACGTCGACGCGCGGCGCAGCTTTATCACCCGCAACGCCAAGGATGTTCGGTTCCTGGATGTCTAACGCAACCCTGCGTTCGATTGCAAACGAGGAATAGATGACAGACACGACGTTGCCGCCTGACG
ACTCGCTCGACCGGATCGAACCGGTTGACATCGAGCAGGAGATGCAGCGCAGCTACATCGACTATGCGATGAGCGTGATCGTCGGCCGCGCGCTGCCGGAGGTGCGCGACGGGCTCAAGCCCGTGCAT
CGCCGGGTGCTCTATGCAATGTTCGATTCCGGCTTCCGCCCGGACCGCAGCCACGCCAAGTCGGCCCGGTCGGTTGCCGAGACCATGGGCAACTACCACCCGCACGGCGACGCGTCGATCTACGACAG
CCTGGTGCGCATGGCCCAGCCCTGGTCGCTGCGCTACCCGCTGGTGGACGGCCAGGGCAACTTCGGCTCGCCAGGCAATGACCCACCGGCGGCGATGAGGTACACCGAAGCCCGGCTGACCCCGTTGG
CGATGGAGATGCTGAGGGAAATCGACGAGGAGACAGTCGATTTCATCCCTAACTACGACGGCCCGGGTGCAAGAGCCGACGGTGCTACCCAGCCGGTTCCCCAACCTGCTGGCCAACGGGTCAGGCGGC
ATCGCGGTCGGCATGGCAACCAATATCCCGCCGCACAACCTGCGTGAGCTGGCCGACGCGGTGTTCTGGGCGCTGGAGAATCACGACGCCGACGAAGAGGAGACCCTGGCCGCGGTCATGGGGCGGGT
TAAAGGCCCGGACTTCCCGACCGCCGGACTGATCGTCGGATCCCAGGGCACCGCTGATGCCTACAAAACTGGCCGCGGCTCCATTCGAATGCGCGGAGTTGTTGAGGTAGAAGAGGATTCCCGCGGTC
GTACCTCGCTGGTGATCACCGAGTTGCCGTATCAGGTCAACCACGACAACTTCATCACTTCGATCGCCGAACAGGTCCGAGACGGCAAGCTGGCCGGCATTTCCAACATTGAGGACCAGTCTAGCGAT
CGGGTCGGTTTACGCATCGTCATCGAGATCAAGCGCGATGCGGTGGCCAAGGTGGTGATCAATAACCTTTACAAGCACACCCAGCTGCAGACCAGCTTTGGCGCCAACATGCTAGCGATCGTCGACGG
GGTGCCGCGCACGCTGCGGCTGGACCAGCTGATCCGCTATTACGTTGACCACCAACTCGACGTCATTGTGCGGCGCACCACCTACCGGCTGCGCAAGGCAAACGAGCGAGCCCACATTCTGCGCGGCC
TGGTTAAAGCGCTCGACGCGCTGGACGAGGTCATTGCACTGATCCGGGCGTCGGAGACCGTCGATATCGCCCGGGCCGGACTGATCGAGCTGCTCGACATCGACGAGATCCAGGCCCAGGCAATCCTG
GACATGCAGTTGCGGCGCCTGGCCGCACTGGAACGCCAGCGCATCATCGACGACCTGGCCAAAATCGAGGCCGAGATCGCCGATCTGGAAGACATCCTGGCAAAACCCGAGCGGCAGCGTGGGATCGT
GCGCGACGAACTCGCCGAAATCGTGGACAGGCACGGCGACGACCGGCGTACCCGGATCATCGCGGCCGACGGAGACGTCAGCGACGAGGATTTGATCGCCCGCGAGGACGTCGTTGTCACTATCACCG
AAACGGGATACGCCAAGCGCACCAAGACCGATCTGTATCGCAGCCAGAAACGCGGCGGCAAGGGCGTGCAGGGTGCGGGGTTGAAGCAGGACGACATCGTCGCGCACTTCTTCGTGTGCTCCACCCAC
GATTTGATCCTGTTCTTCACCACCCAGGGACGGGTTTATCGGGCCAAGGCCTACGACTTGCCCGAGGCCTCCCGGACGGCGCGCGGGCAGCACGTGGCCAACCTGTTAGCCTTCCAGCCCGAGGAACG
CATCGCCCAGGTCATCCAGATTCGCGGCTACACCGACGCCCCGTACCTGGTGCTGGCCACTCGCAACGGGCTGGTGAAAAAGTCCAAGCTGACCGACTTCGACTCCAATCGCTCGGGCGGAATCGTGG
CGGTCAACCTGCGCGACAACGACGAGCTGGTCGGTGCGGTGCTGTGTTCGGCCGGCGACGACCTGCTGCTGGTCTCGGCCAACGGGCAGTCCATCAGGTTCTCGGCGACCGACGAGGCGCTGCGGCCA
ATGGGTCGTGCCACCTCGGGTGTGCAGGGCATGCGGTTCAATATCGACGACCGGCTGCTGTCGCTGAACGTCGTGCGTGAAGGCACCTATCTGCTGGTGGCGACGTCAGGGGGCTATGCGAAACGTAC
CGCGATCGAGGAATACCCGGTACAGGGCCGCGGCGGTAAAGGTGTGCTGACGGTCATGTACGACCGCCGGCGCGGCAGGTTGGTTGGGGCGTTGATTGTCGACGACGACAGCGAGCTGTATGCCGTCA
CTTCCGGCGGTGGCGTGATCCGCACCGCGGCACGCCAGGTTCGCAAGGCGGGACGGCAGACCAAGGGTGTTCGGTTGATGAATCTGGGCGAGGGCGACACACTGTTGGCCATCGCGCGCAACGCCGAA
GAAAGTGGCGACGATAATGCCGTGGACGCCAACGGCGCAGACCAGACGGGCAATTAATCAGGCTCGCCCGACGACGATGCGGATCGCGTAGCGATCTGAGGAGGAATCGGGCAGCTAGGCTCGGCAGC
CGGGTACGAGTGTTAGGAGTCGGGGTGAC (SEQ ID NO: 30)

FIG. 4

Primer Pair #1:

TB.GyrA, Forward1: CTAAGCAACCCTGGTGTCGAT (22 bases) (SEQ ID NO: 31)

TB.GyrA, Reverse1: ATTCCTCCTAGATGCTACG (21 bases) (SEQ ID NO: 32)

Amplicon: 2605 bp

Primer Pair #2:

TB.GyrA, Forward2: AAGGAGTGTGGTTCGTGGAT (21 bases) (SEQ ID NO: 9)

TB.GyrA, Reverse2: TAACATGTAGCCGCT (18 bases) (SEQ ID NO: 10)

Amplicon: 2703 bp

FQ resistance is at codons 94 (Green) and perhaps 90.

TB.GyrA, Reverse3: CGTCGTAGTTAGGG

Mycobacterium tuberculosis H37Ra, complete genome

GenBank: CP000611.1 catalase-peroxidase-peroxynitritase T katG

GTCTTGCGGGGTTATCGCCGATGTCGACTGTGCTGTTGGCGAGGCACCCTGTCTGACGGCCTCGGACCATAACGGCTTCCTGTTGGACGAGGCGGAGGTCATCTACTGGGGTCTATGTCCTGATTGTT
CGATATCCGACACTTCGCGATCACATCCGTGATCACAGCCCGATAACACCAACTCCTGGAAGGAATGCTGTGCCCGAGCAACACCCACCCATTACAGAAACCACCACCGGAGCCGCTAGCAACGGCTG
TCCCGTCGTGGGTCATATGAAATACCCCGTCGAGGGCGGCGGAAACCAGGACTGGTGGCCCAACCGGCTCAATCTGAAGGTACTGCACCAAAACCCGGCCGTCGCTGACCCGATGGGTGCGGCGTTCG
ACTATGCCGCGGAGGTCGCGACCATCGACGTTGACGCCCTGACGCGGGACATCGAGGAAGTGATGACCACCTCGCAGCCGTGGTGGCCCGCCGACTACGGCCACTACGGGCCGCTGTTTATCCGGATG
GCGTGGCACGCTGCCGGCACCTACCGCATCCACGACGGCCGCGGCGGCGCCGGGGGCGGCATGCAGCGGTTCGCGCCGCTTAACAGCTGGCCCGACAACGCCAGCTTGGACAAGGCGCGCCGGCTGCT
GTGGCCGGTCAAGAAGAAGTACGGCAAGAAGCTCTCATGGGCGGACCTGATTGTTTTCGCCGGCAACTGCGCGCTGGAATCGATGGGCTTCAAGACGTTCGGGTTCGGCTTCGGCCGGGTCGACCAGT
GGGAGCCCGATGAGGTCTATTGGGGCAAGGAAGCCACCTGGCTCGGCGATGAGCGTTACAGCGGTAAGCGGGATCTGGAGAACCCGCTGGCCGCGGTGCAGATGGGGCTGATCTACGTGAACCCGGAG
GGGCCGAACGGCAACCCGGACCCCATGGCCGCGGCGGTCGACATTCGCGAGACGTTTCGGCGCATGGCCATGAACGACGTCGAAACAGCGGCGCTGATCGTCGGCGGTCACACTTTCGGTAAGACCCA
TGGCGCCGGCCCGGCCGATCTGGTCGGCCCCGAACCCGAGGCTGCTCCGCTGGAGCAGATGGGCTTGGGCTGGAAGAGCTCGTATGGCACCGGAACCGGTAAGGACGCGATCACCAGCGGCATCGAGG
TCGTATGGACGAACACCCCGACGAAATGGGACAACAGTTTCCTCGAGATCCTGTACGGCTACGAGTGGGAGCTGACGAAGAGCCCTGCTGGCGCTTGGCAATACACCGCCAAGGACGGCGCCGGTGCC
GGCACCATCCCGGACCCGTTCGGCGGGCCAGGGCGCTCCCCGACGATGCTGGCCACTGACCTCTCGCTGCGGGTGGATCCGATCTATGAGCGGATCACGCGTCGCTGGCTGGAACACCCCGAGGAATT
GGCCGACGAGTTCGCCAAGGCCTGGTACAAGCTGATCCACCGAGACATGGGTCCCGTTGCGAGATACCTTGGGCCGCTGGTCCCCAAGCAGACCCTGCTGTGGCAGGATCCGGTCCCTGCGGTCAGCC
ACGACCTCGTCGGCGAAGCCGAGATTGCCAGCCTTAAGAGCCAGATCCGGGCATCGGGATTGACTGTCTCACAGCTAGTTTCGACCGCATGGGCGGCGGCGTCGTCGTTCCGTGGTAGCGACAAGCGC
GGCGGCGCCAACGGTGGTCGCATCCGCCTGCAGCCACAAGTCGGGTGGGAGGTCAACGACCCCGACGGGGATCTGCGCAAGGTCATTCGCACCCTGGAAGAGATCCAGGAGTCATTCAACTCCGCGGC
GCCGGGGAACATCAAAGTGTCCTTCGCCGACCTCGTCGTGCTCGGTGGCTGTGCCGCCATAGAGAAAGCAGCAAAGGCGGCTGGCCACAACATCACGGTGCCCTTCACCCCGGGCCGCACGGATGCGT
CGCAGGAACAAACCGACGTGGAATCCTTTGCCGTGCTGGAGCCCAAGGCAGATGGCTTCCGAAACTACCTCGGAAAGGGCAACCCGTTGCCGGCCGAGTACATGCTGCTCGACAAGGCGAACCTGCTT
ACGCTCAGTGCCCCTGAGATGACGGTGCTGGTAGGTGGCCTGCGCGTCCTCGGCGCAAACTACAAGCGCTTACCGCTGGGCGTGTTCACCGAGGCCTCCGAGTCACTGACCAACGACTTCTTCGTGAA
CCTGCTCGACATGGGTATCACCTGGGAGCCCTCGCCAGCAGATGACGGGACCTACCAGGGCAAGGATGGCAGTGGCAAGGTGAAGTGGACCGGCAGCCGCGTGGACCTGGTCTTCGGGTCCAACTCGG
AGTTGCGGGCGCTTGTCGAGGTCTATGGCGCCGATGACGCGCAGCCGAAGTTCGTGCAGGACTTCGTCGCTGCCTGGGACAAGGTGATGAACCTCGACAGGTTCGACGTGCGCTGATTCGGGTTGATC
GGCCCTGCCCGCCGATCAACCACAACCCGCCGCAGCACCCCGCGAGCTGACCGGCTCGCGGGGTGCTGGTGTTTGCCCGGCGCGATTTGTCAGACCCCGCGTGCATGGTGGTCGCAGGCACGACGAGA
CGGGGATGACGAGACGGGGATGAGGAGAAAGGGCGCCGAAATGTGCTGGATGTGCGATCACCCGGAAGCCACCGCCGAGG (SEQ ID NO: 34)

TB.KatG-Forward1: TCGCGATCACATCCGTGATCAC (SEQ ID NO: 35)

TB.KatG-Reverse1: ATGCACGCGGGGTCTGACAAAT (SEQ ID NO: 36)

Amplicon Size: 2538 bp

FIG. 5

TB-KatG-Forward2: ACACCAACTCCTGGAAGGAAT (SEQ ID NO: 37) or ACACCAACTCCTGGAAGGAAT (SEQ ID NO: 5)

TB-KatG-Reverse2: TGATCGAATNCAGCAGATNA (SEQ ID NO: 6)

Amplicon Size: 2447 bp

The mutation is at Codon 315.

IN Wildtype it is Serine (S)

IN Beijing it is Gycine (G)

In others it is a Threonine (T)

New primers

TB.KatG-Forward3: TTACAGCGGTAAGCGGGATCT (SEQ ID NO: 38)

TB.KatG-Reverse3: TTGCCGAACTCGTCGGCCAATT (SEQ ID NO: 39)

Amplicon size: 603 bp

FIG. 5
Continue

INFLUENZA A (H3N2) MASTER PRIMER LIST FOR ION TORRENT

| | SEQ ID NO: | LENGTH (bp) | MELTING TEMP C | G/C % | AMPL LENGTH (bp) | START POSITION | END POSITION |
|---|---|---|---|---|---|---|---|
| PB2 PRIMER SETS: | | | | | | | |
| FORWARD: ATT ATA TTC AGT ATG GAA AGA A | 40 | 22 | 44.5 | 22.7 | 943 | 1 | 943 |
| REVERSE: ATA TAT CCA CAG CTT GTT C | 41 | 19 | 46.6 | 36.8 | | | |
| | | | | | | | |
| FORWARD: GAT CCA CTA GCA TCT TTA TT | 42 | 20 | 46.9 | 35 | 997 | 835 | 1831 |
| REVERSE: GTA CGT CTC TCA TTT GT | 43 | 18 | 46.5 | 38.9 | | | |
| | | | | | | | |
| FORWARD: AAG GCA TTT TCA GAA AGA T | 44 | 19 | 47 | 31.6 | 998 | 1336 | 2314 |
| REVERSE: GTC GTT TTT AAA CTA TTC AGC | 45 | 21 | 47.7 | 33.3 | | | |
| | AVERAGE: | | 46.5 | | 979 | | |
| PB1 PRIMER SETS: | | | | | | | |
| FORWARD: ACC ATT TGA ATG GAT GTC | 46 | 18 | 47.2 | 38.9 | 996 | 1 | 996 |
| REVERSE: TTG ATT CTT TGT GAT GTA TGT | 47 | 21 | 47.5 | 28.6 | | | |
| | | | | | | | |
| FORWARD: AAT GAT GAC TAA TTC ACA AG | 48 | 20 | 45.3 | 30 | 997 | 997 | 1869 |
| REVERSE: ATA ATT CTC ATC CAT CAG C | 49 | 19 | 46.7 | 36.8 | | | |
| | | | | | | | |
| FORWARD: AAA TAC ACC AAG ACA ACA TA | 50 | 20 | 46.6 | 30 | 1009 | 1316 | 2311 |
| REVERSE: CAT GAA GGA CAA GGT AAA T | 51 | 19 | 47.4 | 36.8 | | | |
| | | | | | | | |
| FORWARD: ATT TTG AAT GGA TGT CAA TC | 52 | 20 | 46.2 | 30 | 913 | 3 | 916 |
| REVERSE: GTG ATT GTG AAA GAA AGC T | 53 | 19 | 48.1 | 36.8 | | | |
| | AVERAGE: | | 46.8 | | 1001 | | |
| PA PRIMER SETS: | | | | | | | |
| FORWARD: CTG ATT CGA AAT GGA AGA | 54 | 18 | 46.6 | 38.9 | 989 | 1 | 989 |
| REVERSE: CGT GTG GTT TGA CTA TAT | 55 | 18 | 46.3 | 38.9 | | | |
| | | | | | | | |
| FORWARD: GAT CAA GTG CAT AAA AAC AT | 56 | 20 | 46.5 | 36.8 | 1001 | 931 | 1931 |
| REVERSE: ATA GAG TCC TAC AGA CTT T | 57 | 19 | | | | | |
| | | | | | | | |
| FORWARD: TGA CGA ACC TGA ATT AAG | 58 | 18 | 46.5 | 38.9 | 998 | 1212 | 2192 |
| REVERSE: GTA CGG ATA ACA AAT AGT AG | 59 | 20 | 44.9 | 35 | | | |
| | AVERAGE: | | 46.2 | | 996 | | |

FIG. 10

| HA PRIMER SETS: | | | | | | |
|---|---|---|---|---|---|---|
| FORWARD: TAA TTC TAT TAA CCA TGA AGA C | 60 | 22 | 45.5 | 27.3 | 887 | 1 |
| REVERSE: GCA TCT GAT CTC ATT ATT G | 61 | 19 | 45.5 | 36.8 | 887 | |
| FORWARD: CAT ACT ACT TTT GAT TAA CAG CA | 62 | 20 | 45.8 | 30 | 940 | 802 |
| REVERSE: TTA ATG CAC TCA AAT GCA | 63 | 18 | 47.1 | 33.3 | 1722 | |
| | | AVERAGE: | 46.0 | | 914 | |
| NP PRIMER SETS: | | | | | | |
| FORWARD: AAT AAT CAC TCA CTG AGT G | 64 | 19 | 46.5 | 36.8 | 803 | 1 |
| REVERSE: AAT ATG AGA TCT TGA TC | 65 | 20 | 46.1 | 35 | 803 | |
| FORWARD: ACA AGA AGT GCT TAT GAG | 66 | 18 | 46.5 | 38.9 | 859 | 690 |
| REVERSE: TTC CTT AAT TGT CGT ACT C | 67 | 19 | 46.4 | 36.8 | 1537 | |
| FORWARD: CTG AGT GAC ATC AAA ATC A | 68 | 19 | 47.3 | 36.8 | 719 | 13 |
| REVERSE: GCA GCT GTT TGA AAT TTT C | 69 | 19 | 48.1 | 36.8 | | 731 |
| | | AVERAGE: | 46.4 | | 831 | |
| NA PRIMER SETS: | | | | | | |
| FORWARD: AAG ATG AAT CCA AAC CAA | 70 | 18 | 46.1 | 33.3 | 758 | 1 |
| REVERSE: GTA TCA GCT TTT CCT GAA | 71 | 18 | 46.5 | 38.9 | 758 | |
| FORWARD: GAT AGT GTT GTT TCA TGG | 72 | 18 | 45.3 | 38.9 | 790 | 657 |
| REVERSE: CTA AAA TTG CGA AAG CTT ATA | 73 | 21 | 46.5 | 28.6 | 1429 | |
| | | AVERAGE: | 46.1 | | 774 | |
| M1/M2 PRIMER SETS: | | | | | | |
| FORWARD: ATA TTG AAA GAT GAG CCT T | 74 | 19 | 46 | 31.6 | 999 | 1 |
| REVERSE: TAG TTT TTT ACT CCA ACT CTA | 75 | 21 | 46 | 28.6 | 999 | |
| | | AVERAGE: | 46 | | 999 | |
| NS1/NS2 PRIMER SETS: | | | | | | |
| FORWARD: ACA AAG ACA TAA TGG ATT CT | 76 | 20 | 46.5 | 30 | 863 | 1 |
| REVERSE: GGT GTT TAT CAT CAA ATA AG | 77 | 23 | 46.4 | 26.1 | 863 | |
| | | AVERAGE: | 46.5 | | 863 | |

*FIG. 10 Continue*

Coding region for pncA gene: SHADED

```
GACGGATTTGTCGCTCACTACATCACCGGTGATCTACCCGGTTGGTTGGGTGGGCCGCTCAGCTGGTCAGTCGTCGGGCGGTCGATGACCTATCTGTGGCTGTCGTA
GGCAACTGCCCCGGCAGTCGCCCGAACGTCTGGAACGTATGCTGGACGTATGCCGAGCTATGCCGGTGATGAGTTGATGACCTCGACGAGTCGCCGGACACGAGTCCTGGGCGGGAACCCCCTAGCGGTAACCGGGTGGCGGCCCGC
GCCATCAGCGCCACCTGGCCGAAGCGGCGAAGCTATACCAGGTGGCAACGATCCATGACAAGCGGGGACTATTCCTCGTCGTGGCACCGGCGGCCATATCCGGACTATTCCTCGTCGTGGCACCGGGCAATTG
CGTCAGCGGGTACTCCCGGCAACGACTCGGCAAGAGGACGTACAACGAGCGTACAAGGGTGCTACAACGGTACAACGGTCCGGGCGGTGCCTTGAGGAGAGAGAGAGAGAGA
CACTGTGAATTGGCTGCGGCAAGCGGCGATGAGGTCGAGATCATTGTGTGCCGCCAGAGGGGAGGAGGGGTACTACTACCTCCAACCAGGGTGGTGGTGG
GACCTGACACGGGTGTGTCGCGGATACCACGGCGATCTCGATGGAGTTTGGAGTTGGAGTTGGAGACCCCGGAAGACCCGGAAGACCCGGAGCCGCAGCCTGACCCGCAGCCTGACGGCAGCCTGACGCAGCCTGACGCGGTC
GAGCGCTCGCCAAGCGGGCCGCCGCCGCCGCCGCGGGATATCACGTCCATCGGATCTGGATATCGTCTCCGGC (SEQ ID NO: 78)
```

FIG. 11A

GACGGATTTGTGCTCAC = pncA.P1-Fwd (SEQ ID NO: 79)

AGCCACCCTGCCAGAA = pncA.P1-Rev (SEQ ID NO: 80)

CATCGTCGACGTGCAGAA = pncA.P2-Fwd (SEQ ID NO: 81)

TGTCCAGACTGGGATGGAA = pncA.P2-Rev (SEQ ID NO: 82)

ATTGGCTCAGCGGTACT = pncA.P3-Fwd (SEQ ID NO: 83)

TGGCCAAGCCATTGCGTA = pncA.P3-Rev (SEQ ID NO: 84)

ATCATTGTGTGCGCCAGA = pncA.P4-Fwd (SEQ ID NO: 85)

CAACAGTTCATCCCGGTT = pncA.V2.P4-Rev (SEQ ID NO: 86)

PncA.P1: 221 bp

GACGGATTTGTGCTCACTACTACACCGGGTGATTATCCCGGCGATGGCCTGGTCCGCCCGGCCTCAGCTGGTTGGGTGGCATCGTCGACTGCAGTGTTCGGCGATCGTCGCGGCTGGGTAGTCTGTGGCTGCCTGCCGCGTCGGTA
GGCAAACTGCCCGGCGAGTGCATGCCCGAACGTATGGGATGGGCGGGCTTGATCATCGTCGACGTGCAGAACGGACTACGAGCAGGCAT (SEQ ID NO: 87)

PncA.P2: 245 bp

```
                              SEQUENCE LISTING

<160> NUMBER OF SEQ ID NOS: 90

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tcctctaagg gctctcgtt                                                        19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtcaggtaca cgatctcgt                                                        19

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atcgaaacgc cgtaccgcaa                                                       20

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgacgtcgag cacgtaactc cct                                                   23

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acaccaactc ctgggaagga at                                                    22

<210> SEQ ID NO 6
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 6
tgatcgcaca tccagcacat tt                                              22

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gacggatttg tcgctcacta c                                               21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gccggagacg atatccagat                                                 20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aaggatgttc ggttcctgga t                                               21

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
taacactcgt acccggct                                                   18

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ttctaaatac ctttggctcc ct                                              22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
```

```
        primer

<400> SEQUENCE: 12
tggccaactt tgttgtcatg ca                                              22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acgcgtgatc agcaaaagca gg                                              22

<210> SEQ ID NO 14
<211> LENGTH: 1161
<212> TYPE: DNA
<213> ORGANISM: Mycobacterium tuberculosis

<400> SEQUENCE: 14
aggcgggaat gaacaccgtc acagccgagt ccatcgcgac ctcgagttcg agatcgcgca     60
gcaccaccgt gccggagacg atatccagat cgcgatggaa cgtgatatcc cgcggcccga    120
tgaaggtgtc gtagaagcgg ccgatggcct catgccccac ctgcggctgc gaacccaccg    180
ggtcttcgac ccgcgcgtca ccggtgaaca acccgaccca gccggcgcgg tcgtgcgcgg    240
cggccgcttg cggcgagcgc tccaccgccg ccaacagttc atcccggttc ggcggtgcca    300
tcaggagctg caaaccaact cgacgctggc ggtgcgcatc tcctccagcg cggcgacggt    360
ggtatcggcc gacacacccg ctgtcaggtc caccagcacc ctggtggcca agccattgcg    420
taccgcgtcc tcggccgtct ggcgcacaca atgatcggtg caataccga ccacatcgac     480 ctcatcgacg ccgcgttgcc gcagccaatt cagcagtggc gtgccgttct cgtcgactcc    540
ttcgaagccg ctgtacgctc cggtgtaggc acccttgtag aacaccgcct cgattgccga    600
cgtgtccaga ctgggatgga agtccgcgcc gggagtaccg ctgacgcaat gcggtggcca    660
cgacgaggaa tagtccggtg tgccggagaa gtggtcaccc gggtcgatgt ggaagtcctt    720
ggttgccacg acgtgatggt agtccgccgc ttcggccagg tagtcgctga tggcgcgggc    780
cagcgcggcg ccaccggtta ccgccagcga gccacccctcg cagaagtcgt tctgcacgtc    840
gacgatgatc aacgcccgca tacgtccacc atacgttcgg gcgactgccc gggcagtttg    900
cctaccgacg cggcagccac agatatagg tccatgacgc cgcgacgatc gcgaacatga     960
ccagctgagc ggcggccacc caaccggcgg gatagatcac gccggtgatg tagtgagcga   1020
caaatccgtc cggtgacaga ggtgtcatcg cggccttggt gcgagccag cgctccaccc    1080 aggtcagcgg gcagtcgacc cgcttagcgg cgatgccgat cccccatatc accgccggaa   1140
catgcagcca catcgtgcgt c                                             1161

<210> SEQ ID NO 15
<211> LENGTH: 1161
<212> TYPE: DNA
<213> ORGANISM: Mycobacterium tuberculosis

<400> SEQUENCE: 15
gacgcacgat gtggctgcat gttccggcgg tgatatgggg gatcggcatc gccgctaagc     60
gggtcgactg cccgctgacc tgggtggagc gctgggctcg caccaaggcc gcgatgacac    120
```

```
ctctgtcacc ggacggattt gtcgctcact acatcaccgg cgtgatctat cccgccggtt    180
gggtggccgc cgctcagctg gtcatgttcg cgatcgtcgc ggcgtcatgg accctatatc    240
tgtggctgcc gcgtcggtag gcaaactgcc cgggcagtcg cccgaacgta tggtggacgt    300
atgcgggcgt tgatcatcgt cgacgtgcag aacgacttct gcgagggtgg ctcgctggcg    360
gtaaccggtg gcgccgcgct ggcccgcgcc atcagcgact acctggccga agcggcggac    420
taccatcacg tcgtggcaac caaggacttc cacatcgacc cgggtgacca cttctccggc    480
acaccggact attcctcgtc gtggccaccg cattgcgtca gcggtactcc cggcgcggac    540
ttccatccca gtctggacac gtcggcaatc gaggcggtgt tctacaaggg tgcctacacc    600
ggagcgtaca gcggcttcga aggagtcgac gagaacggca cgccactgct gaattggctg    660
cggcaacgcg cgtcgatga ggtcgatgtg gtcggtattg ccaccgatca ttgtgtgcgc    720
cagacggccg aggacgcggt acgcaatggc ttggccacca gggtgctggt ggacctgaca    780
gcgggtgtgt cggccgatac caccgtcgcc gcgctggagg agatgcgcac cgccagcgtc    840
gagttggttt gcagctcctg atggcaccgc cgaaccggga tgaactgttg gcggcggtgg    900
agcgctcgcc gcaagcggcc gccgcgcacg accgcgccgg ctgggtcggg ttgttcaccg    960
gtgacgcgcg ggtcgaagac ccggtggggtt cgcagccgca ggtggggcat gaggccatcg   1020
gccgcttcta cgacaccttc atcgggccgc gggatatcac gttccatcgc gatctggata   1080
tcgtctccgg cacggtggtg ctgcgcgatc tcgaactcga ggtcgcgatg gactcggctg   1140
tgacggtgtt cattcccgcc t                                              1161
```

<210> SEQ ID NO 16
<211> LENGTH: 186
<212> TYPE: PRT
<213> ORGANISM: Mycobacterium tuberculosis

<400> SEQUENCE: 16

```
Met Arg Ala Leu Ile Ile Val Asp Val Gln Asn Asp Phe Cys Glu Gly
1               5                   10                  15

Gly Ser Leu Ala Val Thr Gly Gly Ala Ala Leu Ala Arg Ala Ile Ser
            20                  25                  30

Asp Tyr Leu Ala Glu Ala Ala Asp Tyr His His Val Ala Thr Lys
        35                  40                  45

Asp Phe His Ile Asp Pro Gly Asp His Phe Ser Gly Thr Pro Asp Tyr
    50                  55                  60

Ser Ser Ser Trp Pro Pro His Cys Val Ser Gly Thr Pro Gly Ala Asp
65                  70                  75                  80

Phe His Pro Ser Leu Asp Thr Ser Ala Ile Glu Ala Val Phe Tyr Lys
                85                  90                  95

Gly Ala Tyr Thr Gly Ala Tyr Ser Gly Phe Glu Gly Val Asp Glu Asn
            100                 105                 110

Gly Thr Pro Leu Leu Asn Trp Leu Arg Gln Arg Gly Val Asp Glu Val
        115                 120                 125

Asp Val Val Gly Ile Ala Thr Asp His Cys Val Arg Gln Thr Ala Glu
    130                 135                 140

Asp Ala Val Arg Asn Gly Leu Ala Thr Arg Val Leu Val Asp Leu Thr
145                 150                 155                 160

Ala Gly Val Ser Ala Asp Thr Thr Val Ala Ala Leu Glu Glu Met Arg
                165                 170                 175

Thr Ala Ser Val Glu Leu Val Cys Ser Ser
            180                 185
```

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 17
tcatggaccc tatatctgtg 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 18
atgaactgtt ggcggcggtg 20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 19
acggatttgt cgctcactac 20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 20
atctggatat cgtctccggc 20

<210> SEQ ID NO 21
<211> LENGTH: 1737
<212> TYPE: DNA
<213> ORGANISM: Mycobacterium tuberculosis

<400> SEQUENCE: 21
ggccatgctc ttgatgcccc gttgtcgggg gcgtggccgt ttgttttgtc aggatatttc 60
taaatacctt tggctccctt ttccaaaggg agtgtttggg ttttgtttgg agagtttgat 120
cctggctcag gacgaacgct ggcggcgtgc ttaacacatg caagtcgaac ggaaaggtct 180
cttcggagat actcgagtgg cgaacgggtg agtaacacgt gggtgatctg ccctgcactt 240
cgggataagc ctgggaaact gggtctaata ccggatagga ccacgggatg catgtcttgt 300
ggtggaaagc gctttagcgg tgtgggatga gcccgcggcc tatcagcttg ttggtggggt 360
gacggcctac caaggcgacg acgggtagcc ggcctgagag ggtgtccggc cacactggga 420
ctgagatacg gcccagactc ctacgggagg cagcagtggg gaatattgca caatgggcgc 480
aagcctgatg cagcgacgcc gcgtggggga tgacggcctt cgggttgtaa acctctttca 540

```
ccatcgacga aggtccgggt tctctcggat tgacggtagg tggagaagaa gcaccggcca      600
actacgtgcc agcagccgcg gtaatacgta gggtgcgagc gttgtccgga attactgggc      660
gtaaagagct cgtaggtggt ttgtcgcgtt gttcgtgaaa tctcacggct taactgtgag      720
cgtgcgggcg atacgggcag actagagtac tgcaggggag actggaattc ctggtgtagc      780
ggtggaatgc gcagatatca ggaggaacac cggtggcgaa ggcgggtctc tgggcagtaa      840
ctgacgctga ggagcgaaag cgtggggagc gaacaggatt agatacgctg gtagtccacg      900
ccgtaaacgg tgggtactag gtgtgggttt ccttccttgg gatccgtgcc gtagctaacg      960
cattaagtac cccgcctggg gagtacggcc gcaaggctaa aactcaaagg aattgacggg     1020
ggcccgcaca agcggcggag catgtggatt aattcgatgc aacgcgaaga accttacctg     1080
ggtttgacat gcacaggacg cgtctagaga taggcgttcc cttgtggcct gtgtgcaggt     1140
ggtgcatggc tgtcgtcagc tcgtgtcgtg agatgttggg ttaagtcccg caacgagcgc     1200 aaccctgtc tcatgttgcc agcacgtaat ggtggggact cgtgagagac tgccggggtc      1260
aactcggagg aaggtgggga tgacgtcaag tcatcatgcc ccttatgtcc agggcttcac     1320
acatgctaca atggccggta caaagggctg cgatgccgcg aggttaagcg aatccttaaa     1380
agccggtctc agttcggatc ggggtctgca actcgacccc gtgaagtcgg agtcgctagt     1440
aatcgcagat cagcaacgct gcggtgaata cgttcccggg ccttgtacac accgcccgtc     1500
acgtcatgaa agtcggtaac acccgaagcc agtggcctaa ccctcgggag ggagctgtcg     1560
aaggtgggat cggcgattgg gacgaagtcg taacaaggta gccgtaccgg aaggtgcggc     1620
tggatcacct cctttctaag gagcaccacg aaaacgcccc aactggtggg gcgtaggccg     1680
tgaggggttc ttgtctgtag tgggcgagag ccgggtgcat gacaacaaag ttggcca       1737
```

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

```
tggccgtttg ttttgtcagg at                                                22
```

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

```
tacagacaag aacccctcac gg                                                22
```

<210> SEQ ID NO 24
<211> LENGTH: 1773
<212> TYPE: DNA
<213> ORGANISM: Mycobacterium tuberculosis

<400> SEQUENCE: 24

```
gatccggaca gatcgttcgc cggccgaaac cgacaaaatt atcgcggcga acgggcccgt       60
gggcaccgct cctctaaggg ctctcgttgg tcgcatgaag tgctggaagg atgcatcttg      120
gcagattccc gccagagcaa aacagccgct agtcctagtc cgagtcgccc gcaaagttcc      180
```

```
tcgaataact ccgtacccgg agcgccaaac cgggtctcct tcgctaagct gcgcgaacca      240
cttgaggttc cgggactcct tgacgtccag accgattcgt tcgagtggct gatcggttcg      300
ccgcgctggc gcgaatccgc cgccgagcgg ggtgatgtca acccagtggg tggcctggaa      360
gaggtgctct acgagctgtc tccgatcgag acttctccg ggtcgatgtc gttgtcgttc       420
tctgaccctc gtttcgacga tgtcaaggca cccgtcgacg agtgcaaaga caaggacatg      480
acgtacgcgg ctccactgtt cgtcaccgcc gagttcatca acaacaacac cggtgagatc      540
aagagtcaga cggtgttcat gggtgacttc ccgatgatga ccgagaaggg cacgttcatc      600
atcaacggga ccgagcgtgt ggtggtcagc cagctggtgc ggtcgcccgg ggtgtacttc      660
gacgagacca ttgacaagtc caccgacaag acgctgcaca gcgtcaaggt gatcccgagc      720
cgcggcgcgt ggctcgagtt tgacgtcgac aagcgcgaca ccgtcggcgt gcgcatcgac      780
cgcaaacgcc ggcaaccggt caccgtgctg ctcaaggcgc tgggctggac cagcgagcag      840
attgtcgagc ggttcgggtt ctccgagatc atgcgatcga cgctggagaa ggacaacacc      900
gtcggcaccg acgaggcgct gttggacatc taccgcaagc tgcgtccggg cgagccccg      960 accaaagagt cagcgcagac gctgttggaa aacttgttct tcaaggagaa gcgctacgac     1020
ctggcccgcg tcggtcgcta aaggtcaac aagaagctcg ggctgcatgt cggcgagccc      1080
atcacgtcgt cgacgctgac cgaagaagac gtcgtggcca ccatcgaata tctggtccgc     1140
ttgcacgagg gtcagaccac gatgaccgtt ccgggcggcg tcgaggtgcc ggtggaaacc     1200
gacgacatcg accacttcgg caaccgccgc ctgcgtacgg tcggcgagct gatccaaaac     1260
cagatccggg tcggcatgtc gcggatggag cgggtggtcc gggagcggat gaccacccag     1320
gacgtggagg cgatcacacc gcagacgttg atcaacatcc ggccggtggt cgccgcgatc     1380
aaggagttct tcggcaccag ccagctgagc caattcatgg accagaacaa cccgctgtcg     1440
gggttgaccc acaagcgccg actgtcggcg ctggggcccg gcggtctgtc acgtgagcgt     1500
gccgggctgg aggtccgcga cgtgcacccg tcgcactacg gccggatgtg cccgatcgaa     1560 accccctgagg ggcccaacat cggtctgatc ggctcgctgt cggtgtacgc gcgggtcaac    1620
ccgttcgggt tcatcgaaac gccgtaccgc aaggtggtcg acggcgtggt tagcgacgag     1680
atcgtgtacc tgaccgccga cgaggaggac cgccacgtgg tggcacaggc caattcgccg     1740
atcgatgcgg acggtcgctt cgtcgagccg cgc                                  1773
```

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
accgacaaaa ttatcgcggc ga                                                 22

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
atcgatcggc gaattggcct gt                                              22
```

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

```
tcgccgcgat caaggagt                                                   18
```

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
tggaggtccg cgacgtgca                                                  19
```

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
aatatctggt ccgcttgcac ga                                              22
```

<210> SEQ ID NO 30
<211> LENGTH: 2717
<212> TYPE: DNA
<213> ORGANISM: Mycobacterium tuberculosis

<400> SEQUENCE: 30

```
gacgtcgacg cgcggcgcag ctttatcacc cgcaacgcca aggatgttcg gttcctggat     60
gtctaacgca accctgcgtt cgattgcaaa cgaggaatag atgacagaca cgacgttgcc    120
gcctgacgac tcgctcgacc ggatcgaacc ggttgacatc gagcaggaga tgcagcgcag    180
ctacatcgac tatgcgatga gcgtgatcgt cggccgcgcg ctgccggagg tgcgcgacgg    240
gctcaagccc gtgcatcgcc gggtgctcta tgcaatgttc gattccggct tccgcccgga    300
ccgcagccac gccaagtcgg cccggtcggt tgccgagacc atgggcaact accacccgca    360
cggcgacgcg tcgatctacg acagcctggt gcgcatggcc cagccctggt cgctgcgcta    420
cccgctggtg gacggccagg gcaacttcgg ctcgccaggc aatgacccac cggcggcgat    480
gaggtacacc gaagcccggc tgaccccgtt ggcgatggag atgctgaggg aaatcgacga    540
ggagacagtc gatttcatcc ctaactacga cggccgggtg caagagccga cggtgctacc    600
cagccggttc cccaacctgc tggccaacgg gtcaggcggc atcgcggtcg gcatggcaac    660
caatatcccg ccgcacaacc tgcgtgagct ggccgacgcg gtgttctggg cgctggaaaa    720
tcacgacgcc gacgaagagg agaccctggc cgcggtcatg gggcgggtta aaggcccgga    780
cttcccgacc gccggactga tcgtcggatc ccagggcacc gctgatgcct acaaaactgg    840
ccgcggctcc attcgaatgc gcggagttgt tgaggtagaa gaggattccc gcggtcgtac    900
```

```
ctcgctggtg atcaccgagt tgccgtatca ggtcaaccac gacaacttca tcacttcgat      960
cgccgaacag gtccgagacg gcaagctggc cggcatttcc aacattgagg accagtctag     1020
cgatcgggtc ggtttacgca tcgtcatcga gatcaagcgc gatgcggtgg ccaaggtggt     1080
gatcaataac ctttacaagc acacccagct gcagaccagc tttggcgcca acatgctagc     1140
gatcgtcgac ggggtgccgc gcacgctgcg gctggaccag ctgatccgct attacgttga     1200
ccaccaactc gacgtcattg tgcggcgcac cacctaccgg ctgcgcaagg caaacgagcg     1260
agcccacatt ctgcgcggcc tggttaaagc gctcgacgcg ctggacgagg tcattgcact     1320
gatccgggcg tcggagaccg tcgatatcgc ccgggccgga ctgatcgagc tgctcgacat     1380
cgacgagatc caggcccagg caatcctgga catgcagttg cggcgcctgg ccgcactgga     1440
acgccagcgc atcatcgacg acctggccaa aatcgaggcc gagatcgccg atctggaaga     1500
catcctggca aaacccgagc ggcagcgtgg gatcgtgcgc gacgaactcg ccgaaatcgt     1560
ggacaggcac ggcgacgacc ggcgtacccg gatcatcgcg gccgacggag acgtcagcga     1620
cgaggatttg atcgcccgcg aggacgtcgt tgtcactatc accgaaacgg atacgccaa     1680
gcgcaccaag accgatctgt atcgcagcca gaaacgcggc ggcaagggcg tgcagggtgc     1740
ggggttgaag caggacgaca tcgtcgcgca cttcttcgtg tgctccaccc acgatttgat     1800
cctgttcttc accacccagg acgggttta tcgggccaag gcctacgact tgcccgaggc     1860
ctcccggacg gcgcgcgggc agcacgtggc caacctgtta gccttccagc ccgaggaacg     1920
catcgcccag gtcatccaga ttcgcggcta caccgacgcc ccgtacctgg tgctggccac     1980
tcgcaacggg ctggtgaaaa agtccaagct gaccgacttc gactccaatc gctcgggcgg     2040
aatcgtggcg gtcaacctgc gcgacaacga cgagctggtc ggtgcggtgc tgtgttcggc     2100
cggcgacgac ctgctgctgg tctcggccaa cgggcagtcc atcaggttct cggcgaccga     2160
cgaggcgctg cggccaatgg gtcgtgccac ctcgggtgtg cagggcatgc ggttcaatat     2220
cgacgaccgc tgctgtcgc tgaacgtcgt gcgtgaaggc acctatctgc tggtggcgac     2280
gtcaggggggc tatgcgaaac gtaccgcgat cgaggaatac ccggtacagg gccgcggcgg     2340
taaaggtgtg ctgacggtca tgtacgaccg ccggcgcggc aggttggttg gggcgttgat     2400
tgtcgacgac gacagcgagc tgtatgccgt cacttccggc ggtggcgtga tccgcaccgc     2460
ggcacgccag gttcgcaagg cgggacggca gaccaagggt gttcggttga tgaatctggg     2520
cgagggcgac acactgttgg ccatcgcgcg caacgccgaa gaaagtggcg acgataatgc     2580
cgtggacgcc aacggcgcag accagacggg caattaatca ggctcgcccg acgacgatgc     2640
ggatcgcgta gcgatctgag gaggaatcgg gcagctaggc tcggcagccg ggtacgagtg     2700
ttaggagtcg gggtgac                                                     2717
```

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
ctaacgcaac cctgcgttcg at       22

<210> SEQ ID NO 32
<211> LENGTH: 21
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 32
attcctcctc agatcgctac g                                                  21

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cgtcgtagtt agggatgaaa tc                                                 22

<210> SEQ ID NO 34
<211> LENGTH: 2640
<212> TYPE: DNA
<213> ORGANISM: Mycobacterium tuberculosis

<400> SEQUENCE: 34
gtcttgcggg gttatcgccg atgtcgactg tgctgttggc gaggcaccct gtctgacggc        60
ctcggaccat aacggcttcc tgttggacga ggcggaggtc atctactggg gtctatgtcc       120
tgattgttcg atatccgaca cttcgcgatc acatccgtga tcacagcccg ataacaccaa       180
ctcctggaag gaatgctgtg cccgagcaac acccacccat tacagaaacc accaccggag       240
ccgctagcaa cggctgtccc gtcgtgggtc atatgaaata ccccgtcgag ggcggcggaa       300
accaggactg tggcccaac cggctcaatc tgaaggtact gcaccaaaac ccggccgtcg        360
ctgacccgat gggtgcggcg ttcgactatg ccgcggaggt cgcgaccatc gacgttgacg       420
ccctgacgcg gacatcgag gaagtgatga ccacctcgca gccgtggtgg cccgccgact        480
acggccacta cgggccgctg tttatccgga tggcgtggca cgctgccggc acctaccgca       540
tccacgacgg ccgcggcggc gccggggcg gcatgcagcg gttcgcgccg cttaacagct        600
ggcccgacaa cgccagcttg gacaaggcgc gccggctgct gtggccggtc aagaagaagt       660
acggcaagaa gctctcatgg gcggacctga ttgttttcgc cggcaactgc gcgctggaat       720
cgatgggctt caagacgttc gggttcggct tcggccgggt cgaccagtgg gagcccgatg       780
aggtctattg gggcaaggaa gccacctggc tcggcgatga cgttacagc ggtaagcggg        840 atctggagaa cccgctggcc gcggtgcaga tggggctgat ctacgtgaac ccggaggggc       900
cgaacggcaa cccggacccc atggccgcgg cggtcgacat cgcgagacg tttcggcgca        960 tggccatgaa cgacgtcgaa acagcggcgc tgatcgtcgg cggtcacact ttcggtaaga      1020
cccatggcgc cggccggcc gatctggtcg gccccgaacc cgaggctgct ccgctggagc       1080
agatgggctt gggctggaag agctcgtatg caccggaaac cggtaaggac gcgatcacca      1140
gcggcatcga ggtcgtatgg acgaacaccc cgacgaaatg ggacaacagt ttcctcgaga      1200
tcctgtacgg ctacgagtgg gagctgacga agagccctgc tggcgcttgg caatacaccg      1260
ccaaggacgg cgccggtgcc ggcaccatcc cggaccgtt cggcgggcca gggcgctccc      1320
cgacgatgct ggccactgac ctctcgctgc gggtggatcc gatctatgag cggatcacgc      1380
gtcgctggct ggaacacccc gaggaattgg ccgacgagtt cgccaaggcc tggtacaagc      1440
tgatccaccg agacatgggt cccgttgcga gataccttgg gccgctggtc cccaagcaga      1500
```

```
ccctgctgtg gcaggatccg gtccctgcgg tcagccacga cctcgtcggc gaagccgaga    1560
ttgccagcct taagagccag atccgggcat cgggattgac tgtctcacag ctagtttcga    1620
ccgcatgggc ggcggcgtcg tcgttccgtg gtagcgacaa gcgcggcggc gccaacggtg    1680
gtcgcatccg cctgcagcca caagtcgggt gggaggtcaa cgaccccgac ggggatctgc    1740
gcaaggtcat tcgcaccctg gaagagatcc aggagtcatt caactccgcg cgccggggga    1800
acatcaaagt gtccttcgcc gacctcgtcg tgctcggtgg ctgtgccgcc atagagaaag    1860
cagcaaaggc ggctggccac aacatcacgg tgcccttcac cccgggccgc acggatgcgt    1920
cgcaggaaca aaccgacgtg gaatcctttg ccgtgctgga gcccaaggca gatggcttcc    1980
gaaactacct cggaaagggc aacccgttgc cggccgagta catgctgctc gacaaggcga    2040
acctgcttac gctcagtgcc cctgagatga cggtgctggt aggtggcctg cgcgtcctcg    2100
gcgcaaacta caagcgctta ccgctgggcg tgttcaccga ggcctccgag tcactgacca    2160
acgacttctt cgtgaacctg ctcgacatgg gtatcacctg ggagccctcg ccagcagatg    2220
acgggaccta ccagggcaag gatggcagtg gcaaggtgaa gtggaccggc agccgcgtgg    2280
acctggtctt cgggtccaac tcggagttgc gggcgcttgt cgaggtctat ggcgccgatg    2340
acgcgcagcc gaagttcgtg caggacttcg tcgctgcctg ggacaaggtg atgaacctcg    2400
acaggttcga cgtgcgctga ttcgggttga tcggccctgc ccgccgatca accacaaccc    2460
gccgcagcac cccgcgagct gaccggctcg cggggtgctg gtgtttgccc ggcgcgattt    2520
gtcagacccc gcgtgcatgg tggtcgcagg cacgacgaga cggggatgac gagacgggga    2580
tgaggagaaa gggcgccgaa atgtgctgga tgtgcgatca cccggaagcc accgccgagg    2640
```

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tcgcgatcac atccgtgatc ac                                              22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
atgcacgcgg ggtctgacaa at                                              22

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
acaccaactc ctggaaggaa t                                               21

```
<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ttacagcggt aagcgggatc t                                            21

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ttggcgaact cgtcggccaa tt                                           22

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
attatattca gtatggaaag aa                                           22

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
atatatccac agcttgttc                                               19

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gatccactag catctttatt                                              20

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gtacgtctct catttgtt                                                18

<210> SEQ ID NO 44
```

<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
aaggcatttt cagaaagat                                                    19

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gtcgttttta aactattcag c                                                 21

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
accatttgaa tggatgtc                                                     18

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ttgattcttt gtgatgtatg t                                                 21

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
aatgatgact aattcacaag                                                   20

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ataattctca tccatcagc                                                    19

<210> SEQ ID NO 50
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
aaatacacca agacaacata                                                    20

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
catgaaggac aagctaaat                                                     19

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
attttgaatg gatgtcaatc                                                    20

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gtgattgtga aagaaagct                                                     19

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ctgattcgaa atggaaga                                                      18

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cgtgtggttt gactatat                                                      18

<210> SEQ ID NO 56
<211> LENGTH: 20
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 56
gatcaagtgc ataaaaacat                                          20

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
atagagtcct acagacttt                                           19

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
tgacgaacct gaattaag                                            18

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
gtacggataa caaatagtag                                          20

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
taattctatt aaccatgaag ac                                       22

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
gcatctgatc tcattattg                                           19

<210> SEQ ID NO 62
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 62 catactttg attaacagca                                                    20

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ttaatgcact caaatgca                                                     18

<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
aataatcact cactgagtg                                                    19

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
aatatgagat cttcgatctc                                                   20

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
acaagaagtg cttatgag                                                     18

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ttccttaatt gtcgtactc                                                    19

<210> SEQ ID NO 68
<211> LENGTH: 19
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 68
ctgagtgaca tcaaaatca                                              19

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gcagctgttt gaaattttc                                              19

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
aagatgaatc caaaccaa                                               18

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gtatcagctt ttcctgaa                                               18

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gatagtgttg tttcatgg                                               18

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ctaaaattgc gaaagcttat a                                           21

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
atattgaaag atgagcctt                                              19

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75 tagttttta ctccaactct a                                            21

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
acaaagacat aatggattct                                             20

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77 ggtgttttt atcatcaaat aag                                          23

<210> SEQ ID NO 78
<211> LENGTH: 960
<212> TYPE: DNA
<213> ORGANISM: Mycobacterium tuberculosis

<400> SEQUENCE: 78
gacggatttg tcgctcacta catcaccggc gtgatctatc ccgccggttg ggtggccgcc    60
gctcagctgg tcatgttcgc gatcgtcgcg gcgtcatgga ccctatatct gtggctgccg   120
cgtcggtagg caaactgccc gggcagtcgc ccgaacgtat ggtggacgta tgcgggcgtt   180
gatcatcgtc gacgtgcaga acgacttctg cgagggtggc tcgctggcgg taaccggtgg   240
cgccgcgctg gcccgcgcca tcagcgacta cctggccgaa cgcgcggact accatcacgt   300
cgtggcaacc aaggacttcc acatcgaccc gggtgaccac ttctccggca caccggacta   360
ttcctcgtcg tggccaccgc attgcgtcag cggtactccc ggcgcggact ccatcccag   420 tctggacacg tcggcaatcg aggcggtgtt ctacaagggt gcctacaccg agcgtacag   480 cggcttcgaa ggagtcgacg agaacggcac gccactgctg aattggctgc ggcaacgcgg   540
cgtcgatgag gtcgatgtgg tcggtattgc caccgatcat tgtgtgcgcc agacggccga   600
ggacgcggta cgcaatggct tggccaccag ggtgctggtg gacctgacag cgggtgtgtc   660
ggccgatacc accgtcgccg cgctggagga gatgcgcacc gccagcgtcg agttggtttg   720
cagctcctga tggcaccgcc gaaccgggat gaactgttgg cggcggtgga gcgctcgccg   780
caagcggccg ccgcgcacga ccgcgccggc tgggtcgggt tgttcaccgg tgacgcgcgg    840
gtcgaagacc cggtgggttc gcagccgcag gtggggcatg aggccatcgg ccgcttctac    900
gacaccttca tcgggccgcg ggatatcacg ttccatcgcg atctggatat cgtctccggc    960

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gacggatttg tcgctcac                                                   18

<210> SEQ ID NO 80
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
agccaccctc gcagaa                                                     16

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
catcgtcgac gtgcagaa                                                   18

<210> SEQ ID NO 82
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tgtccagact gggatggaa                                                  19

<210> SEQ ID NO 83
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
attgcgtcag cggtact                                                    17

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tggccaagcc attgcgta                                                    18

<210> SEQ ID NO 85
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
atcattgtgt gcgccaga                                                    18

<210> SEQ ID NO 86
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
caacagttca tcccggtt                                                    18

<210> SEQ ID NO 87
<211> LENGTH: 221
<212> TYPE: DNA
<213> ORGANISM: Mycobacterium tuberculosis

<400> SEQUENCE: 87
gacggatttg tcgctcacta catcaccggc gtgatctatc ccgccggttg ggtggccgcc      60
gctcagctgg tcatgttcgc gatcgtcgcg gcgtcatgga ccctatatct gtggctgccg     120
cgtcggtagg caaactgccc gggcagtcgc ccgaacgtat ggtggacgta tgcgggcgtt     180
gatcatcgtc gacgtgcaga acgacttctg cgagggtggc t                        221

<210> SEQ ID NO 88
<211> LENGTH: 245
<212> TYPE: DNA
<213> ORGANISM: Mycobacterium tuberculosis

<400> SEQUENCE: 88
catcgtcgac gtgcagaacg acttctgcga gggtggctcg ctggcggtaa ccggtggcgc      60
cgcgctggcc cgcgccatca gcgactacct ggccgaagcg gcggactacc atcacgtcgt     120
ggcaaccaag gacttccaca tcgacccggg tgaccacttc tccggcacac cggactattc     180
ctcgtcgtgg ccaccgcatt gcgtcagcgg tactcccggc gcggacttcc atcccagtct     240
ggaca                                                                 245

<210> SEQ ID NO 89
<211> LENGTH: 246
<212> TYPE: DNA
<213> ORGANISM: Mycobacterium tuberculosis

<400> SEQUENCE: 89
attgcgtcag cggtactccc ggcgcggact tccatcccag tctggacacg tcggcaatcg      60
aggcggtgtt ctacaagggt gcctacaccg gagcgtacag cggcttcgaa ggagtcgacg     120
agaacggcac gccactgctg aattggctgc ggcaacgcgg cgtcgatgag gtcgatgtgg     180

-continued

```
tcggtattgc caccgatcat tgtgtgcgcc agacggccga ggacgcggta cgcaatggct      240
tggcca                                                                246

<210> SEQ ID NO 90
<211> LENGTH: 184
<212> TYPE: DNA
<213> ORGANISM: Mycobacterium tuberculosis

<400> SEQUENCE: 90
atcattgtgt gcgccagacg gccgaggacg cggtacgcaa tggcttggcc accagggtgc      60
tggtggacct gacagcgggt gtgtcggccg ataccaccgt cgccgcgctg gaggagatgc     120
gcaccgccag cgtcgagttg gtttgcagct cctgatggca ccgccgaacc gggatgaact     180
gttg                                                                 184
```

NEXT GENERATION GENOMIC SEQUENCING METHODS

REFERENCE TO RELATED APPLICATIONS

This application is a continuation of U.S. application Ser. No. 14/527,281 filed Oct. 29, 2014, which issued as U.S. Pat. No. 9,598,737 Mar. 21, 2017, and claims priority to U.S. Provisional Application No. 61/897,015 entitled "Ion Torrent Genomic Sequencing Methods" filed Oct. 29, 2013, and is a continuation-in-part of U.S. application Ser. No. 13/890,512 entitled "Ion Torrent Genomic Sequencing" filed May 9, 2013, which issued as U.S. Pat. No. 9,365,904 Jun. 14, 2016 and claims priority to U.S. Provisional Application No. 61/737,250 entitled "Ion Torrent Genomic Sequencing" filed Dec. 14, 2012, U.S. Provisional Application No. 61/695,960 entitled "Ion Torrent Genomic Sequencing" filed Aug. 31, 2012, U.S. Provisional Application No. 61/646,060 entitled "Drug Susceptibility Determination by Ion Torrent Sequencing" filed May 11, 2012, and U.S. Provisional Application No. 61/644,876 "Drug Susceptibility Determination by Ion Torrent Sequencing" filed May 9, 2012, and the entirety of each of which is specifically incorporated by reference.

SEQUENCE LISTING

The instant application contains a Sequence Listing which has been submitted in ASCII format via EFS-Web and is hereby incorporated by reference in its entirety. Said ASCII copy, created on May 7, 2013, is named 3022.019.US_SL.txt and is 37,929 bytes in size.

BACKGROUND

1. Field of the Invention

This invention is directed to tools, compositions and methods for identifying genetic mutation and mega-bases of nucleic acid information by sequencing and, in particular, to electronic media and programs for analyzing sequences, genes and complete genomes by sequencing, and to the mutations identified and kits comprising reagents for identifying mutations in biological samples.

2. Description of the Background

*Mycobacterium tuberculosis* (MTB), the causative agent for *tuberculosis*, is a highly transmissible bacterial pathogen with significant morbidity and mortality, particularly in HIV infected patients. Since 1997 *tuberculosis* has remained the leading cause of death in South Africa, a statistic linked to this country's growing HIV epidemic. Moreover, effective treatment measures in patients with active MTB have been exacerbated by increasing cases of multidrug resistance (MDR) and extensively drug-resistant (XDR) clinical isolates. Microscopy remains the cornerstone for diagnosing MTB in many low resource areas of the world where both MTB and also HIV are prevalent. However, many HIV infected patients with MTB are smear negative and microscopy provides no information about antibiotic resistance. The emergence of multidrug-resistant (MDR) and extensively drug-resistant strains (XDR) has rendered standard MTB treatment regimens ineffective. According to one study, approximately 20% of TB patients in South Africa with HIV have MDR MTB. Rapid detection of MTB and initiating effective therapy is critical to decrease transmission and improve treatment outcome. The roll-out of Cephiad's Gene Xpert (Xpert) has improved MTB diagnosis and provides evidence of Rifampin resistance, but information about other drugs is not provided. Furthermore, it may not be feasible to place Xpert testing in many microscopy labs in low resource settings. The ability to efficiently ship sputum samples centrally for next-generation sequencing (NGS) offers an opportunity to utilize highly trained staff and available infrastructure at central or regional laboratories.

MDR *tuberculosis* strains are resistant to the first line antibiotics rifampin (RIF) and isoniazid (INH), while XDR MTB strains are resistant to both RIF and INH as well as any fluoroquinolone and second-line injectable antibiotic drugs (e.g., amikacin, kanamycin or capreomycin). About 6% of all MTB cases are MDR strains and South Africa continues to report higher percentages of XDR cases each year. While 7% of patients infected with standard MTB strains succumb to infection, the death rate rises to almost 50% with MDR *tuberculosis*. The emergence of antibiotic resistant MTB strains underscores an immediate need for rapid and highly accurate diagnosis, particularly in the developing countries of Africa. In addition, migratory populations make geographical surveillance and tracking of drug resistance strains more urgent.

Culture-based drug susceptibility testing (DST) for MDR strains is considered the gold-standard, but is time consuming (weeks to months), technically challenging and cost prohibitive, especially in resource limited countries. For example, the BACTEC MGIT 960 (Becton Dickinson Microbiology System, Silver Sparks Nev., USA), is an automated continuously culture-based monitoring system that measures bacterial oxygen consumption and can perform DST using prepared kits which are available for susceptibility of strains to a number of antibiotics. DST results obtained with the BACTEC MGIT 960 yield reliable and reproducible but require handling of viable and potentially infectious cultures, days to weeks or delay until results are available, specialized laboratory accommodations and high costs associated with the instrument and consumables.

In recent years, several nucleic acid based assays for determining MTB drug resistance have been developed. One of the most popular commercially available diagnostic assays is the GenoType MTBDRplus Line Probe Assay (LPA) by Hain LifeScience. This test employs nucleic acid extraction, PCR amplification, probe hybridization and colorimetric visualization on lateral strips via an alkaline phosphatase reaction. LPA has been shown to be sensitive and specific, but there are several drawbacks. Sensitivity of the LPA for all resistance-associated mutations will most likely never reach 100% since many mutations that confer resistance have yet to be discovered. Another inherent limitation of the LPA is an inability to detect sample populations that contain a mixture of resistant and susceptible strains. Strains that harbor substitution mutations that change an amino acid to a previously uncharacterized or unknown mutation not presented on the LPA are not detected. Furthermore, the LPA only allows detection of the most frequent mutations that cause resistance. If a strain were to contain mutations outside of the targeted mutations, the wild-type banding pattern will appear leading to a false negative (susceptible) result.

Thus, there is a need for a rapid, standardized, cost-effective protocol for full length gene analysis of critical genes such as, for example, genes associated with first and second line drug resistance.

SUMMARY

The present invention overcomes disadvantages associated with current strategies and designs, and hereby provides tools, compositions, methods to facilitate and simplify sequencing and methods for analyzing sequence information of nucleic acids including full-length genes and complete genomes.

One embodiment of the invention is directed to analyzing drug resistance mutations by semi-conductor sequencing and, preferably, ion torrent sequencing. Nucleic acid segments containing a gene of interest are amplified by PCR and the amplified products are processed and subsequently analyzed by sequencing. For nucleic acid segments that comprise RNA, the RNA is reverse transcribed to DNA. Sequencing is preferably by Ion Torrent, or Next-Generation sequencers including the Ion Torrent Personal Genome Machine (PGM™; Life Technologies). Preferably, the amplification products represent a common full-length, or multiple overlapping pieces of genes of a number of species, strains and/or serotypes of organisms. The amplified products are sequenced and mutations identified and mapped. Mapping identifies both known and previously unknown mutations and is useful to track the progress and movement of drug resistance across a population. Preferably, the invention analyzes nucleic acids of pathogens such as, for example, virus, bacteria or parasites. Preferably the viral pathogens are the causative agents of influenza or HIV and the bacterial pathogens are the causative agents of *tuberculosis*. Ion torrent sequencing of the nucleic acid segments provides enhanced sequencing for rapid, efficient, cost-effective protocol for full length gene analysis. Drug resistance and other mutations are immediately determined.

Another embodiment of the invention is directed to tools, compositions and methods for performing NGS sequencing, preferably ion torrent or MiSeg™ sequencing of genes or complete genomes. The invention comprises obtaining a DNA sequence of an organism of interest and performing polymerase chain reaction analysis using multiple pairs of nucleic acid primers. Each pair of primers is designed to simultaneously amplify overlapping segments of the genome under similar PCR conditions and these may be performed as sequencing reactions or multiplex for multiple genes or the entire genome. Preferred primers possess similar GC content and overall size. A single PCR amplification of the genome produces hundreds of amplification products whose sequences include the full-length gene, large gene and noncoding segments or the entire genome of the organism. These products are analyzed, preferably by NGS, and the sequences matched to create a sequence map of the entire gene or genome.

Another embodiment of the invention is directed to methods of identifying a sequence motif in the genome of a microorganism that confers resistance to an antimicrobial compound, comprising: providing multiple nucleic acid samples obtained from multiple different strains or serotypes of the microorganism; amplifying the sequences of the multiple nucleic acid samples by a polymerase chain reaction; obtaining sequence information of the amplified sequences by ion torrent sequencing; identifying a polymorphism in the genome of at least one microorganism strain or serotype from the sequence information obtained; and correlating the polymorphism identified with a phenotype or genome location of the at least one microorganism strain or serotype to identify the sequence motif that confers resistance to the antimicrobial compound. Preferably, the microorganism is a virus, a *bacterium*, a fungus or a parasite, and the virus is influenza virus and the *bacterium* is *Mycobacterium tuberculosis*. Preferably, the nucleic acid samples are provided in an aqueous molecular transport medium that contains a chaotrope, a detergent, a reducing agent, a chelator, a buffer, and an alcohol, together present in an amount sufficient to lyse cells, denature proteins, inactivate nucleases, kill pathogens, and not degrade nucleic acid. Preferably, amplifying is performed in a one step polymerase chain reaction utilizing a primer pair that amplifies a gene or nucleic acid segment associated with resistance to an antimicrobial compound, and the polymerase chain reaction is carried out in an aqueous mix comprising: a heat-stable polymerase; a mix of deoxynucleotide tri phosphates comprising about equivalent amounts of dATP, dCTP, dGTP and dTTP, a chelating agent, an osmolarity agent, an albumin, a magnesium salt; and a buffer. Preferably the antimicrobial compound is an antibiotic.

Another embodiment of the invention is directed to methods of treating a disease or disorder caused by the at least one microorganism strain or serotype with the antimicrobial compound identified by the methods of the invention. Preferably, treatment comprises the targeted killing of the specific pathogen that is the causative agent of the disease or disorder. Also preferably, the effective dose is determined from methods of the invention by assessing the phenotypic characteristics associated with the target sequence or sequences identified.

Another embodiment of the invention is directed to methods for determining a complete sequence of a genome of an microorganism comprising: producing a series of amplicons by performing a single polymerase chain reaction (PCR) of the genome in an aqueous mixture containing a heat-stable polymerase; a mix of deoxynucleotide tri phosphates comprising about equivalent amounts of dATP, dCTP, dGTP and dTTP; a chelating agent; a salt; a buffer; a stabilizing agent; and a plurality of primer pairs wherein each primer of the plurality of primer pairs has a similar annealing temperatures; sequencing each of the series of amplicons produced by semi-conductor sequencing, and correlating the sequences of the amplicons and constructing the complete sequence of the genome. Preferably, each of the primers of the multiple primer pairs comprise primers that are from 15 to 25 nucleic acids in length and each has a GC content of about 25-50%. Preferably, each primer pair is designed to PCR amplify an amplicon, and the collection of amplicons that are PCR amplified encompass overlapping segment of the complete genome sequence. Preferably, the plurality of primer pairs hybridizes to the genome and are spaced along the genome at about every 500 to 2,000 nucleotides. Preferably, the microorganism is a virus, a *bacterium*, a fungus, a parasite or a cell, and the virus is influenza virus and the *bacterium* is *Mycobacterium tuberculosis*.

Another embodiment of the invention is directed to methods for determining the sequence of a nucleic acid segment in one step comprising: performing a polymerase chain reaction on the nucleic acid segment to produce a series of amplicons, wherein the PCR comprises a heat-stable composition comprising: a polymerase; a mix of deoxynucleotide tri phosphates comprising about equivalent amounts of dATP, dCTP, dGTP and dTTP; a chelating agent; a salt; a buffer; a stabilizing agent; and a plurality of primer pairs wherein each primer of the plurality of primer pairs has an annealing temperature within 5° C.; sequencing each of the series of amplicons produced by semi-conductor sequencing, and correlating the sequences of the amplicons and constructing the sequence of the nucleic acid segment. Preferably the nucleic acid segment is 1 Mb or greater in length, more preferably greater 2 or more Mb in length, more preferably 5 or more Mb in length and more preferably 10 or more Mb in length. Preferably, each of the primers of the multiple primer pairs is of from 16 to 24 nucleotides in length, has a GC content of about 28-35%, and has an annealing temperature of within 3° C. of each other primer. Preferably, each primer pair is designed to PCR amplify an amplicon representing a portion of the sequence of the nucleic acid segment, and the collection of amplicons that are PCR amplified represent overlapping portions of the complete sequence of the segment. Preferably, the plurality of primer pairs hybridizes to the segment at a spacing of about 800 to 1,200 nucleotides in length.

Another embodiment of the invention is directed to mixtures comprising multiple pairs of nucleic acid primers wherein, upon subjecting the collection to a polymerase chain reaction in association with a nucleic acid segment, the collection of primer pairs generates a collection of amplicons, wherein each amplicon is about 500 to 2,000 nucleotides in length, such that the entire sequence of the segment is represented in the resulting collection of amplicons. Preferably, each primer of the collection of primer pairs is about 15 to 25 nucleotides in length, has a GC content of about 25-45%, and an annealing temperature within 3° C. of each other primer, and each primer of the collection of primer pairs contains a sequence that hybridizes to the genome of the same microorganism. Preferably, the microorganism is a virus, a *bacterium*, a parasite, or a fungus. Preferably, the mixture contains a heat-stable polymerase; a mix of deoxynucleotide tri phosphates comprising about equivalent amounts of dATP, dCTP, dGTP and dTTP; a chelating agent; a salt; a buffer; a stabilizing agent and nuclease-free water.

Another embodiment of the invention comprises kits containing reagent vessels preferably including one or more of chemical reagents, primers and polymerases for sequencing. The sample to be analyzed is mixed with a reagent vessel that preferably contains chemical components sufficient to kill all pathogens present in the sample, inactivate nucleases in the sample, and maintain the integrity of the nucleic acids rendering the sample safe for transportation and subsequent manipulation, such as, for example, aqueous lysis buffer, aqueous or anhydrous transport medium, or aqueous PrimeStore Molecular Transport Medium®. The mixture may be combined in a column, such as a microcentrifuge column, which may be included in the kit, to aid in the extraction of nucleic acid form the sample. Extracted nucleic acid is preferably combined with another chemical reagent composition such as, for example PrimeMix® that facilitates nucleic acid testing such as, for example, PCR sequencing. Such reagent composition may contain positive control sequences, negative control sequences and/or sequences that specifically hybridize (under the desired high or low stringency hybridization conditions) to a particular target sequences that is characteristic for the presence of a pathogen.

Another embodiment of the invention is directed to computer-readable media that implements the analytical methods of the invention. Preferable the computer-readable media analyses sequence information obtained and centralizes the collection of information. Also preferably the sequence information is compared with sequence information obtained from one or more known databases of sequence information for the same or similar sequences and identifies mutations that provide antibiotic resistance and other phenotypic characteristics to the microorganism.

Other embodiments and advantages of the invention are set forth in part in the description, which follows, and in part, may be obvious from this description, or may be learned from the practice of the invention.

DESCRIPTION OF THE FIGURES

FIG. 1 Illustrates the pncA gene sequence plus 100 flanking base pairs as well as the reverse compliment sequence, the protein sequence, and the primers sequences.

FIG. 2 Illustrates the nucleotide sequence of H37RV Gene strain as well as the sequences of the TB 16S ribosomal RNA gene sequencing primers.

FIG. 3 Illustrates the rpoB gene conferring sensitivities/resistance to Rifampin as well as the forward and reverse primer sequences for rpoB.

FIG. 4 Illustrates the *Mycobacterium tuberculosis* H37Ra, complete genome (GenBank: CP000611.1) GyrA Gene and three sets of forward and reverse primers.

FIG. 5 *Mycobacterium tuberculosis* H37Ra, complete genome (GenBank: CP000611.1) catalase-peroxidase-peroxynitritase T katG and three sets of forward and reverse primers.

FIG. 6 Illustrates the cycle threshold of Gyrase A and IS 6110 assays.

FIG. 7 Illustrates Gyrase A assay and the IS 6110 assay using sequence isolates by cycle number vs. Ct value.

FIG. 8 Illustrates Gyrase A assay and the IS 6110 assay using sequence isolates vs cycle threshold (ct).

FIG. 9 Summary of results achieved in sequencing the influenza A genome using various primer pair collections with ion torrent sequencing methodology.

FIG. 10 Characterization of primer pairs for whole-genome ion torrent sequencing of influenza A (H3N2).

FIG. 11A Gene sequence of pncA showing coding regions as shaded.

FIG. 11B Gene sequence of pncA forward and reverse primers utilized in PCR tiling and pncA regions P1-P4.

FIG. 12 Architecture of an electronic system of the methods of the invention.

DESCRIPTION OF THE INVENTION

Rapid analysis of genes associated with drug resistant strains is a major challenge for successful treatment of many diseases and disorders. Real-time geographical surveillance of emerging MTB drug resistance would facilitate more appropriate treatment strategies (e.g., drug, antibiotic, chemical). Currently, available molecular methods such as the GenoType® MTBDRplus LPA offer limited detection capabilities, particularly when novel/uncommon amino acid substitutions are within known drug resistance regions or when undiscovered amino acid mutations impact drug resistance. Also, current methodology including Ion Torrent protocol requires multi-steps, ancillary equipment and increased expense, and is labor intensive.

A simplified semiconductor sequencing protocol for rapid characterization of full-length genes and genome has been surprisingly discovered. The invention comprises a standardized protocol for gene sequencing preferably utilizing semiconductor sequencing and preferably Ion Torrent sequencing of full-length genes. The protocol enables sequencing of entire coding regions implemented allowing characterization of known mutations and discovery of new polymorphisms. This protocol also enables the sequencing of mega-bases of nucleotide information such that complete genomes of cells and organisms can be determined and the genetic polymorphism readily mapped and identified. Preferably the cells or organisms are disease causing prokaryotic or eukaryotic cells, or yeast or fungal cells. Preferred disease causing organisms include strains of bacteria, virus, fungus, and parasites. Exemplary organisms include, but are not limited to DNA virus, an RNA virus, a positive or negative single-strand virus, a double strand virus, orthomyxovirus, paramyxovirus, Morbillivirus (e.g., Rubeola), retrovirus, flavivirus, filovirus, lentivirus, hanta virus, herpes virus (e.g., VZV, HSV I, HSV II, EBV), hepatitis virus (e.g., A, B, C, non-A, non-B), Influenza virus (e.g., H5N1, H1N1, H7N9), Respiratory Syncytial Virus, HIV, or Ebola virus. Exemplary organisms also include but are not limited to Mycobacteria (e.g., *M. tuberculosis*), *Bacillus anthracis*, *Plasmodium* (e.g., *Plasmodium falciparum*), Shistosomiasis (e.g., *Schistosoma mansoni*), *Francisella tularensis*, *Clostridium difficile*, Meningococcal infections, *Pseudomonas* infections, *Yersinia pestis*, and *Vibrio cholerae*. The invention is also directed to the detection and characterization of organisms that are related to the pathogenic organisms, but are non-pathogenic. Detection of one or more of the non-pathogenic, but related organisms can be a definitive diagnosis of the absence of disease. In addition, the tools and methods of the invention allow for the identification and characterization of abnormalities in the existing genome of an individual such as a condition that may be present from birth (congenital) and may be heritable. These genetic disorders are equally detectable and characterizable by the tools and methods of the invention and can be diagnosed by comparison with an otherwise normal or control genome of a non-afflicted individual.

Figure 6:
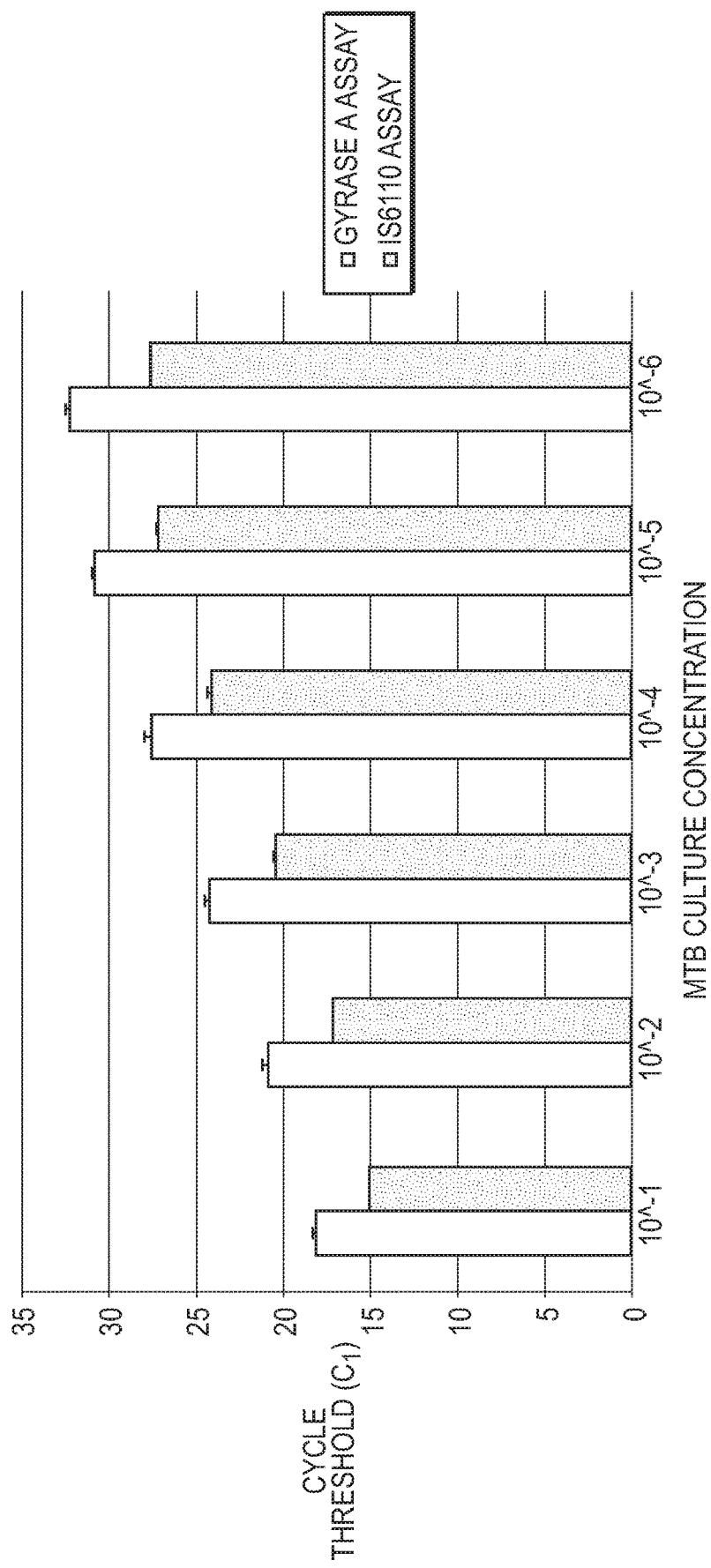

This relatively rapid (e.g., 1, 2, or 3 days, or less), standardized, cost-effective protocol allows for full-length analysis of genes such as, for example, to identify mutations that possess one or more alterations of a DNA, RNA, protein and/or peptide sequence. For sample sequences that are RNA, the RNA sequence of interest in the sample is typically reverse transcribed to DNA for PCR analysis. Preferably identified and characterized are one or more gene mutations that provide a microorganism with resistance to an antibiotic. Preferred mutations that are identified with the methods of the invention are located in one or more sites within an amino acid coding region, a transcription promoter or termination site, a stop or start codon, a site within a non-coding region, a splice junction site, a modification site, a transcription or translation factor binding or recognition site, one or more sites that contribute to a three dimensional structure, or a combination thereof. Preferred genes that are analyzed include MTB genes associated with first and second-line MTB drug resistance (see FIGS. 1-5). Preferred examples of MTB-associated genes include, for example, rpoB (rifampin), katG and inhA (isoniazid), gyrA and gyrB (fluoroquinolones), pncA and panD (PZA or pyrazinamide) and rrs(16s) (aminoglycosides, amikacin, kanamycin, capreomycin, streptomycin) and rspL (streptomycin).

The methods of the invention were used to evaluate 26 geographically diverse clinical isolates collected in South Africa including MDR and XDR strains with next-generation Ion Torrent Personal Genome Machine (PGM). Of particular interest were INDELS, which are insertions or deletions if a single nucleotide (A,T,G,C) causing missense changes in the protein structure. The sequencing data obtained from this developed methodology were compared to the HAIN LPA and genotyping DST data from culture. This methodology for the first time enables sequencing entire coding as well as non-coding regions for genes implemented in resistance allowing characterization of known mutations and discovery of new polymorphisms. Previously uncharacterized substitution mutations were identified on the rrs, rpoB, katG, pncA gyrA and gyr B, katG, inhA and panD genes.

The present invention offers significant potential for new sequencing platforms such as, for example, next-generation instruments to be more utilized in resource deprived environments such as Africa, Asia, and India. Specifically, the current invention improves and streamlines the up-front library preparation process. Methodology of the invention does not require the use of expensive ancillary equipment pieces typically utilized or required by the manufacturer. Specifically, the standardized procedure of the invention does not require an Agilient Bioanalyzer for DNA quantifications; the OneTouch ePCR system for emulsification PCR step, or the PipinPrep for gel excision. Additionally, since the protocol of the invention involves re-sequencing full-coding genes (not necessarily full genomes) the Bioruptor is not required for shearing DNA into smaller pieces. Additionally, it is not necessary to sequence the entire genome and then identify genes. The method and tools of the invention allow for pre-selection of the genes and/or regions of interest that are to be sequenced. As the Agilent 2100 BioAnalyzer, OneTouch, PipinPrep, and Bioruptor all require additional training for use, consume valuable laboratory bench space, and are extremely expensive, the invention represents a significant advance and improvement over convention methodologies.

The sequencing protocol of the invention is exemplified herein using Ion Torrent sequencing as this sequencing method has been applied to *M. tuberculosis*. As believed to clear to those skilled in the art, the protocol involves semiconductor sequencing, with is exemplified by Ion Torrent sequencing and, as such, involves the sequencing of large numbers of different regions simultaneously. The sequencing and nucleic acid methodologies are applicable to any series of genes, genomes or nucleic acid sequences.

The invention also includes a methodology for selecting primer pairs for sequencing a target of interest. Primer pairs are preferably selected with matched annealing and melting temperature as to the target. Preferably, melting and annealing temperatures are based on sequence characteristics such as the GC content of the sequence, the possibility of self-hybridization of the primer (e.g., forming hairpin loops within the primer), and possible structures near the binding site. Preferably the primers do not self-hybridize under the conditions of sequencing. Preferably the GC content of primers is between about 25% and 50%, more preferably between about 30% and 40%, more preferably between about 25% and 35%, and also more preferably between about 40% and 50%. Thus, primer sequences of the target are selected for hybridization based on sequence characteristics such that all of the primer pairs utilized for the target will have similar melting and/or annealing temperatures to the target. Preferably primer sequences contain no regions of reasonably possible self hybridization of the primer sequence. Preferably primer pairs are matched for annealing and/or disassociation temperatures which may be within 5° C., within 4° C., with 3° C., within 2° C., with 1° C. and more preferably the same annealing temperature, the same melting temperature or both. Primer pairs preferably generate amplicons of between about 500 to about 2,000 nucleotides (NT) in length that represent overlapping segment of the target, more preferably between about 600 and 1,500 NT, more preferably between about 700 and 1,300 NT, more preferably between about 800 and 1,200 NT, more preferably between about 900 and 1,100 NT, and more preferably about 1,000 NT. Primers are generally between 12 NT and 45 NT in length, more preferably between 15 and 35 NT, and more preferably between about 18 and 25 NT. Although not a rule, generally longer primers have a lower GC content. Exemplary primers pairs are identified for the pncA gene (see FIG. 1), the H37RV gene strain (see FIG. 2), the rpoB gene (see FIG. 3), the GyrA gene (see FIG. 4, and the katG gene (see FIG. 5). These primer pairs are useful to combine in ready to use kits to simplify the sequencing of full-length genes.

In one embodiment of the invention, a semiconductor sequencing protocol was determined for five genes of *M. tuberculosis* for determining drug resistance in MDR and XDR strains (e.g., cumulatively sequencing 11.4 kb per isolate). The *M. tuberculosis* rpoB gene encodes a 1,178 amino acid beta subunit for an RNA dependent DNA polymerase enzyme. Mutations within an 81-bp "core region" of the rpoB gene are responsible for approximately 95% of rifampin resistance in *M. tuberculosis* strains. Three of these mutations at positions 516 (D→V), 526 (H→Y/D), and 531 (S→L) constitute the majority of mutations within this region. Of the 21 rifampin-resistant strains characterized in this study, 11 (52.4%) carried the S531L mutation, 7 (33.3%) contained an amino acid substitution at position 516, and 3 (14.3%) contained a mutation at position 526 of the rpoB gene (Table 1). The most prevalent rpoB substitution observed at position 516 is a valine (D516V). Ion Torrent sequencing according to the invention revealed that 6 of 7 strains contained a rarer glycine residue (D516G) at this position (Table 1). These 6 strains were shown as absent for both mutant and wild type bands by LPA (Table 1). Similarly an uncommon amino acid substitution was identified at position 526 in the rpoB gene. The most prevalent amino acid substitution reported at position 526 in the rpoB gene is a histidine to tyrosine or aspartic acid (H526Y/D). Ion Torrent sequencing revealed 1 of 3 isolates contained an uncommon arginine (R) residue (H526R) that by HAIN LPA was shown to be absent for both wild type and mutant bands (Table 1). While absence of wild type and mutant bands in a sample are interpreted as resistant according to LPA testing, there remains ambiguity since the type of amino acid change is not directly characterized. This underscores the utility of Ion Torrent sequencing for resistance surveillance, and discovery of novel amino acids in circulating MTB strains.

TABLE 1

Summary of 10 amino acid mutations in the first 900 amino acid residues* of the rpoB gene of 26 (14 MDR, 7 XDR and 5 fully susceptible) *M. tuberculosis* isolates from South Africa deduced by Ion Torrent sequencing, Hain LPA genotyping and culture.

| Isolate No. | Amino Acid Substitution(s)** of rpoB gene (3619 bps) | Rifampin Result by | | |
|---|---|---|---|---|
| | | Ion Torrent* | HAIN LPA | Bacter MGIT 960 |
| 9 | S531L | Resistant | Resistant | Resistant |
| 1 | S531L, V194I | Resistant | Resistant | Resistant |
| 1 | S531L, Y645H | Resistant | Resistant | Resistant |
| 1 | H526D | Resistant | Resistant | Resistant |
| 1 | H526Y, S509R | Resistant | Resistant | Resistant |
| 1 | H526R | Resistant | Resistant | Resistant |
| 5 | wild type** | Sensitive | Sensitive | Sensitive |
| 6 | D516G, L533P | Resistant | Resistant | Resistant |
| 1 | D516V | Resistant | Resistant | Resistant |

*There were 5 rpoB amino acid substitutions (R908C, Q1042H, P1043A, I1187T, and V1249F) noted in at least 1 strain at the 3' end (residues 900-1253).
**Compared to the sequenced H37Rv reference strain.

The katG gene encodes catalase peroxidase, an enzyme that converts isoniazid (INH) into the active form. The majority of isoniazid resistance is associated with katG codon 315 (S315T), although mutations in the promoter region of inhA and nod also contribute to resistance. Of 26 strains assessed, 16 (62%) contained the characteristic serine-to-threonine amino acid substitution at position 315 (S315T) conferring isoniazid resistance (Table 2). These sequencing results exhibited 100% concordance with comparisons made using the HAIN LPA and culture DST.

TABLE 2

Summary of 4 amino acid mutations in the katG gene of 26 (14 MDR, 7 XDR and 5 fully susceptible) *M. tuberculosis* isolates from South Africa deduced by Ion Torrent sequencing, Hain LPA genotyping and culture

| Isolate No. | Amino Acid Substitution(s)** of katG gene (2447 bps) | Rifampin Result by | | |
|---|---|---|---|---|
| | | Ion Torrent* | HAIN LPA | Bacter MGIT 960 |
| 11 | S315T | Resistant | Resistant | Resistant |
| 5 | S315T, R463L | Resistant | Resistant | Resistant |
| 1 | W191R, R463L | Sensitive | Sensitive | Sensitive |
| 7 | wild type** | Sensitive | Sensitive | Sensitive |
| 1 | R463L | Sensitive | Sensitive | Sensitive |
| 1 | N138H | Sensitive | Sensitive | Sensitive |

*Rifampin resistance is known to occur in rpoB at positions 531 (S→T), 526 (H→Y/D), and 516 (D→V).
**Compared to the sequenced H37Rv reference strain.

Pyrazinamide (PZA) is a synthetic derivative of nicotinamide that has been used as a first-line drug to fight *tuberculosis* since 1952. Standard DST for PZA is complicated due to an acidic pH requirement in vitro, which inhibits *M. tuberculosis* growth and complicates accurate phenotypic assessment. PZA resistance is attributed to mutations in the pncA gene which encodes a pyrazinamidase. These resistance conferring mutations are numerous and include amino acid substitutions, frameshifts and stop codon mutations. Seven mutations were characterized from the 26 South African isolates assessed, including one silent mutation, 5 amino acid substitutions, and one chain termination mutation. The Q122 (Stop) termination mutation (Table 3) observed in one isolate is novel, having not been reported elsewhere. The difficulty in PZA phenotypic assessment and the variability of mutations along the pncA gene further underscores the added value of Ion Torrent gene sequencing to assess mutations in this hyper variable MTB gene.

TABLE 3

Summary of 6 amino acid mutations in the pncA gene of 26 (14 MDR, 7 XDR and 5 fully susceptible) M. tuberculosis from South Africa deduced by Ion Torrent sequencing and culture

| Isolate No. | Amino Acid Substitution(s)** in the pncA gene (3619 bps) | Pyrazinamide Result by | |
|---|---|---|---|
| | | Ion Torrent* | Bacter MGIT 960 |
| 3 | C14R | Resistant | Resistant |
| 1 | A102V | Resistant | Resistant |
| 1 | Q122 (stop) | Resistant | Resistant |
| 16 | wild type** | Sensitive | Sensitive |
| 1 | V139G | Resistant | Resistant |
| 1 | R154G | Resistant | Resistant |
| 2 | L172P | Resistant | Resistant |
| 1 | Silent (C195T) | Sensitive | Sensitive |

*pyrazinamide resistance is known to occur in 25 mutations described by Mphahele et al (23).
**Compared to the sequenced H37Rv reference strain. One strain contained a silent (synonymous) nucleotide mutation at position 195 (C→T).

The primary target of fluoroquinolones (FQ) in *M. tuberculosis* is DNA gyrase, a type II topoisomerase composed of two A and B subunits encoded by the gyrA and gyrB genes, respectively. Amino acid substitutions located within a short region of the gyrA gene known as the quinolone resistance-determining region (QRDR), account for the majority of known FQ resistant *tuberculosis* strains. Substitution mutations in the QRDR at positions 88, 90, and 94 were observed in 10 of 26 (38.5%) sequences from this study (Table 4). Three of these 10 strains contained substitutions at position 94 in the gyrA gene; two were noted as D94G substitutions, and one was a D94Y substitution. Both D94G and D94Y have been characterized as substitutions and both amino acid substitutions at codon 94 give rise to similar levels of FQ antibiotic resistance. Of the strains assessed, the gyrA gene was the most variable containing nine amino acid substitutions in the 26 clinical isolates assessed. Furthermore, two of these gyrA codons (549 and 613), exhibited heterogeneous residues (Table 4), an advantage of performing Ion Torrent sequencing over HAIN LPA and DST.

TABLE 4

Summary of 10 amino acid mutations in the gyrA gene of 26 (14 MDR, 7 XDR and 5 fully susceptible) M. tuberculosis isolates from South Africa deduced by Ion Torrent sequencing and culture

| Isolate No. | Amino Acid Substitution(s)** in the gyrA gene (2664 bps) | Rifampin Result by | |
|---|---|---|---|
| | | Ion Torrent* | Bacter MGIT 960 |
| 3 | E21Q, S95T, G2475S, G668D | Sensitive | Sensitive |
| 2 | E21Q, D94G, S95T, G668D | Resistant | Resistant |
| 1 | E21Q, G88C, S95T, G668D | Resistant | Resistant |
| 10 | E21Q, S95T, G668D | Sensitive | Sensitive |
| 1 | wild type** | Sensitive | Sensitive |
| 1 | E21Q, S95T, G668D, Q613Q/E+ | Sensitive | Sensitive |
| 1 | E21Q, S95T, G668D, L5495/L+ | Sensitive | Sensitive |
| 1 | E21Q, D94Y, S95T, G668D | Resistant | Resistant |
| 6 | E21Q, A90V, S95T, G247S, G668D | Resistant | Resistant |

*Fluroquinolone resistance is known to occur in gyrA at position 88 (G→C), 90 (A→V), 91 (S91P) and 94 (D→H).
**Compared to the sequenced H37Rv reference strain.
+There is a heterozygous nucleotide mutation in a proportion of Ion Torrent reads; the mutation confers a mixed amino acid substitution.

Emerging cases of XDR *tuberculosis* defined as MDR cases having acquired additional resistance to FQ, i.e., ofloxacin, and at least one of the three injectable 'second-line drugs', i.e., amikacin (AMK), kanamycin (KAN), or capreomycin (CAP), have become a public health threat in developing countries worldwide. The majority of resistance to second line drugs is associated with mutations in codons 1401 (A1401G), 1402 (C1402T), and 1484 (G1483T) in the 16 S ribosomal RNA rrs gene. Analysis of African MTB strains revealed that 7 of 26 (27%) were defined as XDR as evident by nucleotide mutation at position 1401 (A1401G) (Table 4). Three additional nucleotide mutations at positions 492, 514, and 878 were also discovered (Table 5) in strains from this analysis. The G878A is a novel nucleotide mutation but was shown to be sensitive to AMK, KAN, and CAP according to DST.

TABLE 5

Summary of 4 nucleotide mutations in the rrs (16s) gene of 26 (14 MDR, 7 XDR and 5 fully susceptible) M. tuberculosis isolates from South Africa deduced by Ion Torrent sequencing and culture.

| Isolate No. | Amino Acid Substitution(s)** in the rrs (16s) gene (1680 bps) | Kanamycin Result by | |
|---|---|---|---|
| | | Ion Torrent* | Bacter MGIT 960 |
| 1 | G878A | Sensitive | Sensitive |
| 12 | wild type** | Sensitive | Sensitive |
| 1 | A514C, A1401G | Resistant | Resistant |
| 6 | A1401G | Resistant | Resistant |
| 3 | A514C | Sensitive | Sensitive |
| 1 | C492T | Sensitive | Sensitive |
| 1 | C492T, A514C | Sensitive | Sensitive |
| 1 | A514C | Sensitive | Sensitive |

*Aminoglycoside resistance is known to occur at positions 1401 (A→G), 1402 (C→T), and 1484 (G→T).
**Compared to the sequenced H37Rv reference strain.

Previous studies have shown that mutations in katG codon 463, and gyrA codon 95 are genetic markers for categorizing strains into epidemiological genetic Groups 1, 2, and 3, and that these codons have no effect on antibiotic resistance. Group 1 strains are genetic ancestors of Group 2 and Group 3 strains that link the predominately non-human *mycobacterium* genus (*M. microti* and *M. bovis strains*) with human *M. africanum* and *M. tuberculosis* lineages. As evident by substitution mutations in katG codon 463 and gyrA codon 95, a total of 7 of 26 (27%), 18 of 26 (69%), and 1 of 26 (4%) of the African isolates characterized in this study were members of genetic Group 1, 2, and 3, respectively. Tracking Group 1 organisms is important in terms of MTB detection since several isolates belonging to genetic Group 1 lack Insertion Sequence 1661 (IS-1661), a common genetic target for several PCR-based MTB detection assays.

The Ion Torrent protocol for MTB drug resistance can be easily integrated into low resource settings throughout countries and regions such as Africa, India, and China. The Ion Torrent methodology does not require the use of expensive ancillary equipment such as Agilent 2100 BioAnalyzer, DiaGenode Bioruptor® Sonication System, Ion OneTouch System™, ultracentrifuges, or the Pippin Prep™ Workstation as current Ion Torrent protocols recommend. This is significant since these instruments and needed accessories and consumables can be expensive, require large laboratory footprints, and often require routine maintenance.

In contrast to the GenoType® MTBDRplus or MTBDRs1 Line Probe Assay (LPA), the Ion Torrent PGM protocol provides full-length characterization of genes, making possible discovery of new amino acid substitutions that could potentially be missed by LPA since LPA is limited to only known mutations. Using the protocol, several uncommon amino acid changes in clinical field isolates have been found. Furthermore, the extensive depth of sequence coverage from the Ion Torrent allows for discovery of heterogeneous or mixed strain genetic populations within an isolate.

The scalability of Ion Torrent sequencing permits expansion to include megabases of additional genes on a single chip. The methodology of the invention is expandable beyond the five full-length MTB genes to include all 16 plus genes that currently constitute MTB drug resistance. Full-length gene analysis using the Ion Torrent PGM will identify novel mutations that, when correlated to phenotypic minimal inhibitory concentration (MIC) testing, identify new *tuberculosis* resistant residues as well as the cumulative inhibitory effect of multiple mutations.

Another embodiment of the invention is directed to megabase sequence identification utilizing semiconductor sequencing protocols. Megabase sequencing according to the invention involves selection of primer pairs that amplify different sections of the target sequence whereby the collection of sections represents the entirety of the target sequence. Preferably the sections overlap to a degree that permits alignment of the resulting amplicons forming the complete target sequence. Primer pairs are preferably designed to form amplicons with lengths of about 0.5 k to about 5 k nucleotides, preferably about 0.6 k to about 3 k nucleotides, more preferably about 0.7 k to about 2 k nucleotides, and more preferably about 0.8 k to about 1 k nucleotides. Primer pairs are preferably of similar GC contact such that the annealing or hybridization temperatures are as similar or preferably within about 5° C., more preferably within about 2° C., and more preferably within about 1° C. Also preferred is that the hybridization disassociation temperatures be similar, such that annealing and disassociation occur at very similar temperature for polymerization and PCR. In annealing and disassociation, the length of the primer influences the temperature profile, thus similar length for the all or at least most of the primers is preferred. Primer lengths are preferably about 15-30 nucleotides, more preferably about 20-28 nucleotides, and more preferably about 18 to 25 nucleotides. Although it is preferred that all of the primers have such similar characteristics, megabase sequencing can be performed when greater than about 80% of the primers share one or more characteristics, more preferably 85% or more, more preferably 90% or more, and even more preferably 95% or more. Primer pairs can be assembled into kits to facilitate full-length sequencing. Primers targeted to amplify a target sequence are added to nucleic acid obtained from samples. In accordance with the utilization of such similar primers, a PCR reaction is performed with one target nucleic acid to be amplified with a mixture of all primer pairs. Also preferred is performance of duplicate PCR analysis on identical mixtures. The number of cycles can range from 10 to 50 or more and, preferably temperature cycling is performed in accordance with convention PCR temperature and reaction conditions.

Another embodiment of the invention is directed to methods of treating a disease or disorder caused by the at least one microorganism strain or serotype with the antimicrobial compound identified by the methods of the invention. Preferably, treatment comprises the targeted killing of the specific pathogen that is the causative agent of the disease or disorder. Also preferably, the effective dose is determined from methods of the invention by assessing the phenotypic characteristics associated with the target sequence or sequences identified, and thereby selected known or testing suspected agents for treatment. Preferably, the therapeutically effective dose can be determined from the sequencing information obtained by the sequencing methods of the invention. For example, certain sequences, if determined to be present, are known to cause certain phenotypic characteristics, such as, for example, resistance or sensitivity to certain antibiotics or other therapeutic treatments. The presence or absence of these sequences, as well as the quantity of sequences present, can provide an indication and direction of effective treatment as well as the therapeutically effective dose for treatment.

Another embodiment of the invention comprises kits containing reagent vessels preferably including one or more of chemical reagents, primers and polymerases for sequencing. The sample to be analyzed is mixed with a reagent vessel that preferably contains chemical components sufficient to kill all pathogens present in the sample, inactivate nucleases in the sample, and maintain the integrity of the nucleic acids rendering the sample safe for transportation and subsequent manipulation, such as, for example, aqueous lysis buffer, aqueous or anhydrous transport medium, or aqueous PrimeStore Molecular Transport Medium® (described in U.S. Pat. Nos. 8,084,443, 8,080,645 and 8,097,419, all of which are specifically incorporated by reference). The mixture may be combined in a column, such as a micro-centrifuge column, which may be included in the kit, to aid in the extraction of nucleic acid form the sample. Extracted nucleic acid is preferably combined with another chemical reagent composition such as, for example PrimeMix® (also described in U.S. Patent Publication No. 2011/0281754 entitled "Compositions and Methods for Detecting, Identifying and Quantitating Mycobacterial-Specific Nucleic Acids" filed Apr. 25, 2011, and International Application Publication No. WO2012/149188 entitled "Compositions and Methods for Detecting and Identifying Nucleic Acid Sequences in Biological Samples" filed Apr. 26, 2012, which are both specifically incorporated by reference), that facilitates nucleic acid testing such as, for example, PCR sequencing. Such reagent composition may contain positive control sequences, negative control sequences and/or sequences that specifically hybridize (under the desired high or low stringency hybridization conditions) to a particular target sequences that is characteristic for the presence of a pathogen.

Another embodiment of the invention is directed to computer readable programming that implements the methods of the invention (see FIG. 12). Preferably the computer readable media includes provides formats for including both specific and general information with regard to each sample. That information can be easily centralized and stored. An exemplary electronic system of the method of the invention includes at least one general-purpose computing device 100, including a processing unit (CPU) 120 and a system bus 110 that couples various system components including the system memory such as read only memory (ROM) 140 and random access memory (RAM) 150 to the processing unit 120. Preferably, additional system memory 130 is also available for use. The electronic method may operate on a computing device with more than one CPU 120 or on a group or cluster of computing devices networked together to provide greater processing capability. The system bus 110 may be any of several types of bus structures including a memory bus or memory controller, a peripheral bus, and a local bus using any of a variety of bus architectures. A basic input/output (BIOS) stored in ROM 140 or the like, may provide the basic routine that helps to transfer information between elements within the computing device 100, such as during start-up. The computing device 100 further includes storage devices such as a hard disk drive 160, a magnetic disk drive, an optical disk drive, tape drive or the like. The storage device 160 is connected to the system bus 110 by a drive interface. The drives and the associated computer readable media provide nonvolatile storage of computer readable instructions, data structures, program modules and other data for the computing device 100. The basic components are known to those of skill in the art and appropriate variations are contemplated depending on the type of device, such as whether the device is a small, handheld computing device, a desktop computer, a computer server, a handheld scanning device, or a wireless device, including wireless Personal Digital Assistants ("PDAs"), tablet devices, wireless web-enabled or "smart" phones. Preferably, the system is technology agnostic.

Although the exemplary environment described herein employs the hard disk, other types of computer-readable media that can store data that are accessible by a computer, such as magnetic cassettes, flash memory cards, digital versatile disks, cartridges, random access memories (RAMs), read only memory (ROM), a cable or wireless signal containing a bit stream and the like, may also be used in the exemplary operating environment.

To enable user interaction with the computing device 100, an input device 190 represents any number of input mechanisms, such as a microphone for speech, a touch-sensitive screen for gesture or graphical input, keyboard, mouse, motion input, speech, game console controller, TV remote and so forth. The output device 170 can be one or more of a number of output mechanisms known to those of skill in the art, for example, printers, monitors, projectors, speakers, and plotters. In some embodiments, the output can be via a network interface, for example uploading to a website, emailing, attached to or placed within other electronic files, and sending an SMS or MMS message. In some instances, multimodal systems enable a user to provide multiple types of input to communicate with the computing device 100. The communications interface 180 generally governs and manages the user input and system output. There is no restriction on the invention operating on any particular hardware arrangement and therefore the basic features here may easily be substituted for improved hardware or firmware arrangements as they are developed.

For clarity of explanation, the illustrative system embodiment is presented as comprising individual functional blocks (including functional blocks labeled as a "processor"). The functions these blocks represent may be provided through the use of either shared or dedicated hardware, including, but not limited to, hardware capable of executing software. For example, the functions of one or more processors presented in FIG. 1 may be provided by a single shared processor or multiple processors. (Use of the term "processor" should not be construed to refer exclusively to hardware capable of executing software.) Illustrative embodiments may comprise microprocessor and/or digital signal processor (DSP) hardware, read-only memory (ROM) for storing software performing the operations discussed below, and random access memory (RAM) for storing results. Very large scale integration (VLSI) hardware embodiments, as well as custom VLSI circuitry in combination with a general purpose DSP circuit, may also be provided.

Embodiments within the scope of the present invention may also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, objects, components, and data structures, etc. that performs particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Preferred embodiments of the invention may be practiced in network computing environments with many types of computer system configurations, including personal computers, hand-held devices, multi-processor systems, microprocessor-based or programmable consumer electronics, network PCs, minicomputers, mainframe computers, and the like. Networks may include the Internet, one or more Local Area Networks ("LANs"), one or more Metropolitan Area Networks ("MANs"), one or more Wide Area Networks ("WANs"), one or more Intranets, etc. Embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

Preferably, the computer-readable media is connected to the Internet and can access publically available databases, such as for example, PubMed or GeneBank and retrieve sequence and related information regarding the microorganism being analyzed including the DNA, RNA and/or protein sequence of one or more genes or portions of genes of the microorganism. The sequences being analyzed by, for example, Ion Torrent sequencing is compared with one or more (e.g., 1, $10^1$, $10^2$, $10^3$, $10^4$, $10^5$, $10^6$, $10^7$, or even greater numbers) known sequences of the same or similar microorganism or other synthetic or recombinant sequences. Results achieved can provide a rapid and thorough analysis of the gene or gene portion as compared with dozens, hundreds or even thousands of known sequences. Mutations that represent resistance can be easily and rapidly determined and identified.

The following examples illustrate embodiments of the invention, but should not be viewed as limiting the scope of the invention.

Examples

Clinical Isolates. A total of 26 geographically diverse clinical isolates, representing drug-sensitive, MD, and XDR tuberculosis strains were obtained from sample archives of the University of Pretoria, South Africa, and the National Institute for Communicable Diseases (NICD), Sandringham, South Africa. The H37Rv MTB lab strain was included as a sequencing control throughout the protocol. All MTB isolates used were archived strains from pure culture MGIT™ 960 System tubes (Becton Dickinson, Sparks, Md.) with species identification and genotypic resistance to rifampin and isoniazid determined using the Genotype® MTBDplus assay (HAIN LifeSciences, Germany) according to manufacturer's instructions. Phenotypic resistance for first and second line drugs was performed using the MGIT™ 960 System as previously described. Critical concentrations for ofloxacin and kanamycin (second line drugs) were 2.0 µg/mL and 5.0 µg/mL, respectively. Resistance to first and second line drugs was determined using standard diagnostics algorithms.

DNA preparation. MTB isolates were handled in blinded fashion throughout. MTB samples (0.5 mL) were pipetted into cryovial tubes containing 1.5 mL PrimeStore Molecular Transport Medium® (a molecular transport medium) (Longhorn Vaccines & Diagnostics, San Antonio, Tex.). Inactivated samples were transported from South Africa to San Antonio, Tex., USA at ambient temperature (3-4 days) and stored at 5° C. until used. Total DNA (50 µl) was purified from a 200 µl aliquot of PrimeStore MTM® containing inactivated culture using a Qiagen® EZ1® Advanced Robot and EZ1 DNA Tissue Kit (Cat No. 953034) according to manufacturer's recommendations (Qiagen Inc., Germantown, Md.).

Primer Design. Novel PCR primers were designed for amplification of full-length coding regions for each MTB gene of interest (Table 6).

TABLE 6

PCR amplification primers used for full length analysis of MTB Genes.

| Amplification Target | Forward | Reverse | Amplicon (bp) |
|---|---|---|---|
| rpoB | 5'-TCCTCTAAGGGCTCTCGTT -3' | 19 nt (SEQ ID NO 1) | 1625 |
|  | 5'-GTCAGGTACACGATCTCGT -3' | 19 nt (SEQ ID NO 2) |  |
| rpoBll (2 half) | 5'-ATCGAAACGCCGTACCGCAA -3' | 20 nt (SEQ ID NO 3) | 2056 |
|  | 5'-TGACGTCGAGCACGTAACTCCCT -3' | 23 nt (SEQ ID NO 4) |  |
| katG | 5'-ACACCAACTCCTGGGAAGGAAT -3' | 22 nt (SEQ ID NO 5) | 2447 |
|  | 5'-TGATCGCACATCCAGCACATTT -3' | 22 nt (SEQ ID NO 6) |  |
| pncA | 5'-GACGGATTTGTCGCTCACTAC -3' | 21 nt (SEQ ID NO 7) | 960 |

TABLE 6-continued

PCR amplification primers used for full length analysis of MTB Genes.

| Amplification Target | Forward | Reverse | Amplicon (bp) |
|---|---|---|---|
|  | 5'-GCCGGAGACGATATCCAGAT -3' | 20 nt (SEQ ID NO 8) |  |
| gyrA | 5'-AAGGATGTTCGGTTCCTGGAT -3' | 21 nt (SEQ ID NO 9) | 2664 |
|  | 5'-TAACACTCGTACCCGGCT -3' | 18 nt (SEQ ID NO 10) |  |
| rrs (16s) | 5'-TTCTAAATACCTTTGGCTCCCT -3' | 22 nt (SEQ ID NO 11) | 1680 |
|  | 5'-TGGCCAACTTTGTTGTCATGCA -3' | 22 nt (SEQ ID NO 12) |  |
|  |  | (5 genes) | 11,432 BP total |

Primer pairs for rpoB (2 sets of primers), katG, pncA, gyrA, and rrs (16s) gene amplification were designed using the genome sequence of M. tuberculosis H37Rv strain as reference (GenBank accession no. NC_000962). Primer secondary structure, melting temperature, and potential primer-dimer formation were determined using LaserGene 9.1 (DNAStar, Madison, Wis.) and PrimerExpress 3.0 (Life Technologies, Foster City, Calif.). All oligonucleotides were synthesized using standard, de-salted primers (Integrated DNA Technologies (IDT), San Diego, Calif.).

PCR Amplification. Amplification reactions for all MTB gene targets were designed and optimized to be used under one standardized set of thermocycling parameters. All PCR 'mastermixes' were prepared using Platinum Taq DNA Polymerase, 10× Buffer, and 50 mM $MgCl_2$ (P/N 10966-034; Life Technologies, Foster City, Calif.). Amplification was carried out in a 50 µl final volume reaction mixture containing 24.1 µl Ambion Nuclease-Free Water (Cat No. AM 9932; Life Technologies, Foster City, Calif.), 5 µl 10×PCR Buffer, 2 µl 50 mM $MgCl_2$ (2 mM final), 0.4 µl PCR Nucleotide Mix Ultrapure dNTPS (200 µM final for each dNTP; P/N 77119; USB, Santa Clara, Calif.), 0.5 µl Platinum Taq DNA Polymerase (2.5 Units final), and 2 µl primer blend (rpoB, katG, pncA, gyrA, or rrs genes; 0.4 µM final for each primer). To each 34 µl 'mastermix' reaction mixture, 16 µl extracted DNA was added to bring the total volume to 50 µl. Reactions were carried out in MicroAmp Optical 96-Well Reaction Plates (P/N N801-0560, Life Technologies, Foster City, Calif.) and capped using MicroAmp 8-Cap Strips (P/N 4323032, Life Technologies, Foster City, Calif.). Amplification was performed using an ABI 2720 thermocycler (Life Technologies, Foster City, Calif.). Thermocycling parameters were 95° C. for 2 minutes, followed by 40 cycles at 95° C. for 30 seconds, 55° C. for 15 seconds, and 72° C. for 2 minutes with final extension at 72° C. for 5 minutes. Resulting amplicons were confirmed by addition of 5 µl PCR product with 1 µl GelPilot Loading Dye 5× (P/N 1037649; Qiagen, Germantown, Md.) on 1% (wt/vol) Molecular Biology Grade Agarose (Cat No. BP1356; Fischer Scientific, Pittsburg, Pa.) with ethidium bromide (0.1 µg/mL final; Cat No 161-0433; Bio-Rad, Hercules, Calif.). Electrophoretic separation of products was carried out for 60 minutes at 0.4 mV cm$^2$ in 1× Tris Borate-EDTA (TBE) Buffer (Cat No. 1B70153; IBI Scientific, Peosta, Iowa). Amplicons were visualized under UV transillumination, and size estimation made using a TrackIt 1 kb Plus DNA Ladder (P/N 10488-085; Life Technologies, Foster City, Calif.). After visualization, the remaining PCR reaction for each clinical isolate gene amplification (~45 µL) corresponding to rpoB, katG, pncA, gyrA, and rrs (16s) targets were transferred to a single microcentrifuge tube. Pooled genes corresponding to each clinical isolate were subjected to PCR purification and eluted in 50 µl Low Tris-EDTA (TE) (Cat No. 602-1155-010; Life Technologies, Foster City, Calif.) using the MinElute Reaction Cleanup Kit (Cat No. 28204; Qiagen, Germantown, Md.) according to manufacturer's instructions. The concentration and purity of DNA was determined spectrophotometrically using a NanoDrop ND 1000 (Thermo Fischer Scientific, Wilmington, Del.).

Ion Torrent Library Preparation. Barcoded libraries were generated using the Ion Xpress Plus Fragment Library Kit (Cat No. 4471269, Life Technologies, Foster City, Calif.) and the Ion Xpress DNA Barcoding 1-16 Kit (Cat No. 4468654, Life Technologies, Foster City, Calif.) according to a modified version of the protocol outlined in the Ion Xpress Plus gDNA and Amplicon Library Preparation.

Amplicon Shearing. Chemical shearing was performed using 1-3 µg DNA containing an approximate equimolar pool of rpoB, katG, pncA, gyrA, and rrs (16s) gene amplicons. DNA shearing was performed in a 50 µl total reaction volume by combining 5 µl Ion Shear Plus 10× Reaction Buffer, 10 µl enzyme, and 35 µl pooled DNA template (Ion Xpress Plus Fragment Library Kit, Cat No. 4471269, Life Technologies, Foster City, Calif.). The reaction mixture was incubated at 37° C. for 45 minutes, terminated using 5 µl Ion Shear Stop Buffer, and stored on ice until purification. Sheared DNA was purified using Agencourt Ampure XP-PCR Purification beads (P/N A63880; Beckman Coulter, Brea, Calif.) with Dynal magnetic bead stand (Cat No. 123-21D; Life Technologies, Foster City, Calif.) according to manufacturer's recommendations. Briefly, 99 µl Agencourt beads was mixed with 50 µl ion shear reaction, incubated for 5 minutes at room temperature, placed on a magnetic stand, washed twice with 70% (v/v) ethanol, and eluted using 12 µl Low TE Buffer (Cat No. 602-1155-010; Life Technologies Inc., Foster City, Calif.).

Adaptor Ligation. Adaptor ligation was performed in a 0.2 mL low bind PCR tube (P/N PCR-02-L-C; Axygen Inc., Union City, Calif.) by combining 12 µl sheared amplicon with 1.25 µl Ligase Buffer, 1.25 µl P1-IA Adaptor Mix (Ion DNA Barcoding 1-16 Kit, Cat No. 4468654 Life Technologies, Foster City, Calif.) and 0.2 µl DNA Ligase (Ion Xpress Plus Fragment Library Kit, Cat No. 4471269, Life Technologies, Foster City, Calif.). The mixture was pipetted up and down 5 times and incubated at room temperature (22-25° C.) for 30 minutes. Adaptor ligation reactions were purified and eluted in 10 µl Low TE Buffer using the Agencourt Ampure XP-PCR Purification beads (P/N A63880; Beckman Coulter, Brea, Calif.) with the Dynal magnetic bead stand (Cat No. 123-21D; Life Technologies, Foster City, Calif.) according to manufacturer's recommendations.

Nick Translation and Barcode Amplification. Amplicon pools from each patient sample were barcoded using the Ion DNA Barcoding 1-16 Kit and Ion Xpress Fragment Library Kit (Part Nos. 4468654 and 4471269, respectively; Life Technologies, Foster City, Calif.). To maximize yields reactions were scaled 2× by combining 40 µl Platinum PCR SuperMix High Fidelity, 4.4 µl of Ion Primer Mix (BC X where X=barcode 1-16) and 10 µl of ligated DNA. Amplification was performed using an ABI 2720 thermocycler (Life Technologies, Foster City, Calif.). Thermocycling parameters comprised 72° C. for 20 minutes, 95° C. for 5 minutes, followed by 10 cycles of 95° C. for 15 seconds, 58° C. for 15 seconds and 68° C. for 1 minute. Following amplification, bar-coded samples were purified and eluted in 50 µl of Low TE (Cat No. 602-1155-010; Life Technologies, Foster City, Calif.) using the MinElute Reaction Cleanup Kit (Cat No. 28204; Qiagen, Germantown, Md.) according to manufacturer's instructions. DNA concentration and purity was determined by spectrophotometric analysis using a NanoDrop ND 1000 (Thermo Fischer Scientific, Wilmington, Del.). Ranges for purified bar-coded samples are typically 150-300 ng/µl with A260/280 purity of 1.7-1.9. Equimolar concentrations (~2-3 µg of each bar-coded sample) were combined into a single 1.5 mL nuclease-free microcentrifuge tube and used for size selection.

Size Selection. The appropriate volume of GelPilot 5× Loading Dye (P/N 1037649; Qiagen, Germantown, Md.) was added to the pooled bar-coded MTB library tube and loaded onto a 1% (w/v) agarose gel (Cat No. BP1356; Fischer Scientific, Pittsburg, Pa.) containing ethidium bromide (0.1 µg/mL final; Cat No 161-0433; Bio-Rad, Hercules, Calif.). The bar-coded library was electrophoresed for 60 minutes at 0.4 mV cm$^2$ in 1×TBE Buffer (Cat No. 1B70153; IBI Scientific, Peosta, Iowa) and visualized under UV transillumination. Size estimations were determined using a TrackIt 1 kb Plus DNA Ladder (P/N 10488-085; Life Technologies, Foster City, Calif.). Gel excision was performed under UV transillumination using a sterile scalpel blade excising out a target region between 75-200 bp. Excised agarose gel slices were placed into sterile 1.5 mL microcentrifuge tubes and subjected to DNA purification using the PureLink Quick Gel Extraction Kit (Cat No. K210012; Life Technologies, Foster City, Calif.) according to manufacturer's instructions. Concentration and purity values for the barcoded DNA library were determined spectrophotometrically using a NanoDrop ND 1000 (Thermo Fischer Scientific, Wilmington, Del.). The recommended library input for emulsion PCR is ~140-560×10$^6$ molecules per 18 µl. This range was achieved by a 1:1000 dilution using library stock and nuclease-free water.

Emulsion Polymerase Chain Reaction (emPCR). Emulsion Polymerase chain reaction was performed in a 1 mL reaction volume using the Ion Template Preparation Kit (Cat No. 4469000; Life Technologies, Foster City, Calif.) by adding 582 µl nuclease-free water, 200 µl 5×PCR Reagent Mix, 100 µl 10×PCR Enzyme Mix, 100 µl Ion Sphere Particles, and 18 µl diluted library template. The preparation was mixed thoroughly followed by brief centrifugation in a microcentrifuge. Emulsion was achieved using the Ultra-Turrax Tube Drive (Life Technologies, Foster City, Calif.). A total of 9 mL chilled Emulsion Oil (Ion Torrent Preparation Kit; Cat No. 4469000, Life Technologies, Foster City, Calif.) was added to an Ion Template Preparation Tube (Cat No. 4467226, Life Technologies, Foster City, Calif.). The emulsion tube was placed and locked onto the IKA Ultra-Turrax Tube Drive and initiated. While the tube was in motion, the entire 1 mL PCR master mix solution was dispensed into the cap port and mixed for 5 minutes. The mixed emulsion was transferred to a 96-well PCR plate and amplified using an ABI 2720 thermocycler (Life Technologies, Foster City, Calif.) using the following thermocycling parameters: 94° C. for 6 minutes, followed by 40 cycles at 94° C. for 30 seconds, 58° C. for 30 seconds, and 72° C. for 90 seconds; followed by 5 cycles at 94° C. for 30 seconds, and 68° C. for 6 minutes.

Ion Sphere Particle (ISP) Recovery and Qubit Measurement. Ion Sphere Particles were recovered using reagents supplied in the Ion Xpress Template Kit (Cat No. 4469001, Life Technologies, Foster City, Calif.) according to manufacturer's protocol (Ion Xpress Template Kit User Guide v2.0, pages 18-19). Quantification of recovered particles was performed using a Qubit 2.0 Fluorometer (Life Technologies, Foster City, Calif.) and an Ion Sphere Quality Control Kit (Cat No. 4468656, Life Technologies, Foster City, Calif.) according to manufacturer's recommendations (Ion Xpress Template Kit User Guide, page 25-26). The optimal amount of template-positive ion sphere particles (ISPs) is between 4-50%. Relative fluorescent unit (RFU) values obtained outside of this range were not pursued into subsequent ISP enrichment.

ISP Enrichment. ISPs were enriched using reagents supplied in the Ion Xpress Template Kit, Ion Sequencing Kit, and DynaBeads MyOne Streptavidin C1 beads (Cat Nos. 4469001, 4468997 and 650.01 respectively; Life Technologies, Foster City, Calif.) according to the manufacturer's protocols (Ion Xpress Template Kit User Guide v2.0, pages 15-17).

Ion Torrent 314 Chip Preparation and PGM Sequencing. Ion Torrent 314 Chips (Cat No. 4462923; Life Technologies, Foster City, Calif.) were prepared and loaded according to manufacturer's recommendation (Ion Sequencing Kit User Guide v 2.0). The Ion Torrent PGM was run according to Ion Torrent 314 Chip specifications including a 65-cycle sequencing protocol, use of 18 megaOhm purified water, and standard compressed argon gas to drive fluidics through the PGM system. All rpoB, katG, pncA, gyrA and rrs genes and corresponding proteins were deposited into GenBank (accession numbers JX303203-JX303332).

Figure 7:
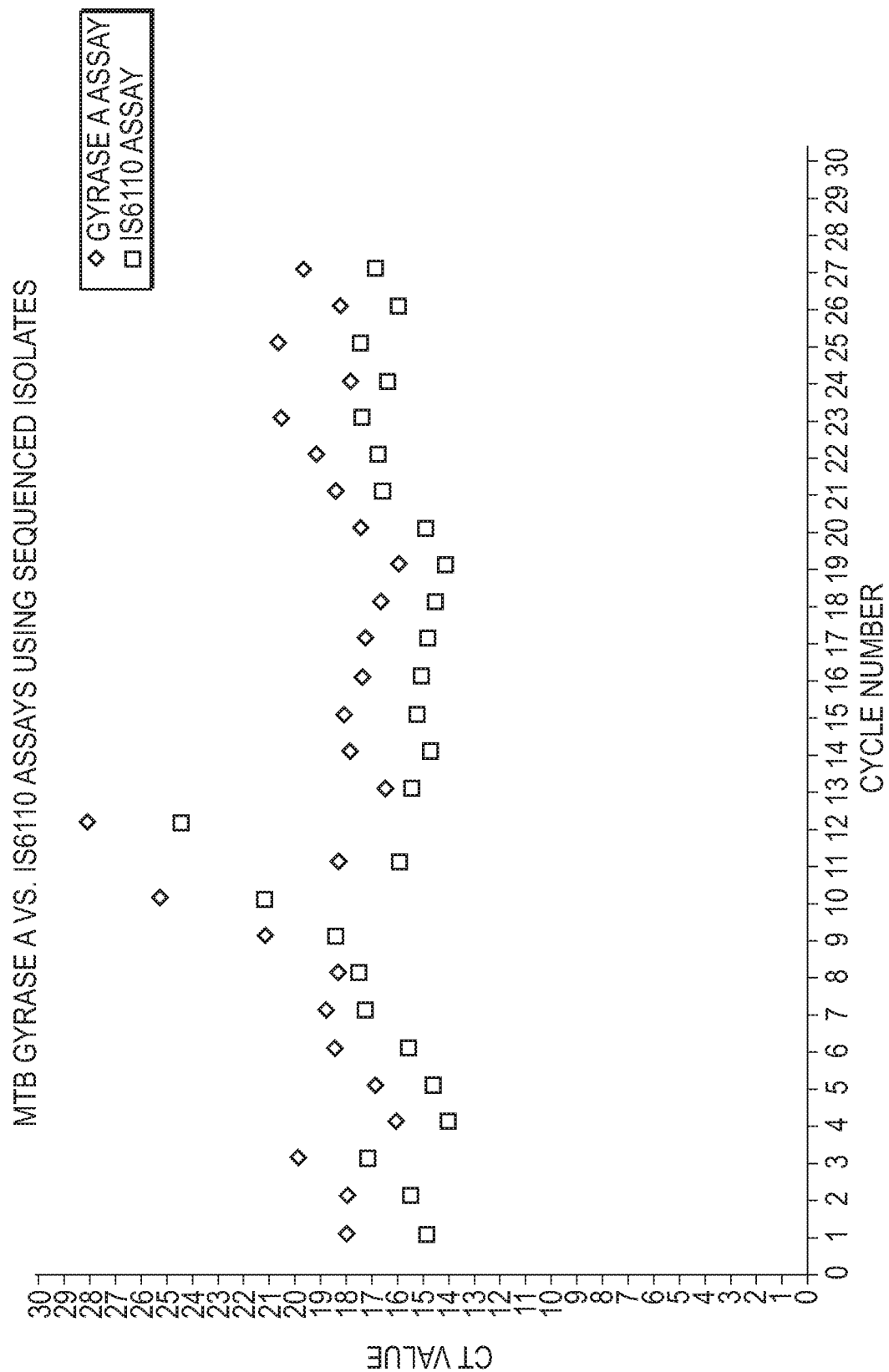
Figure 8:
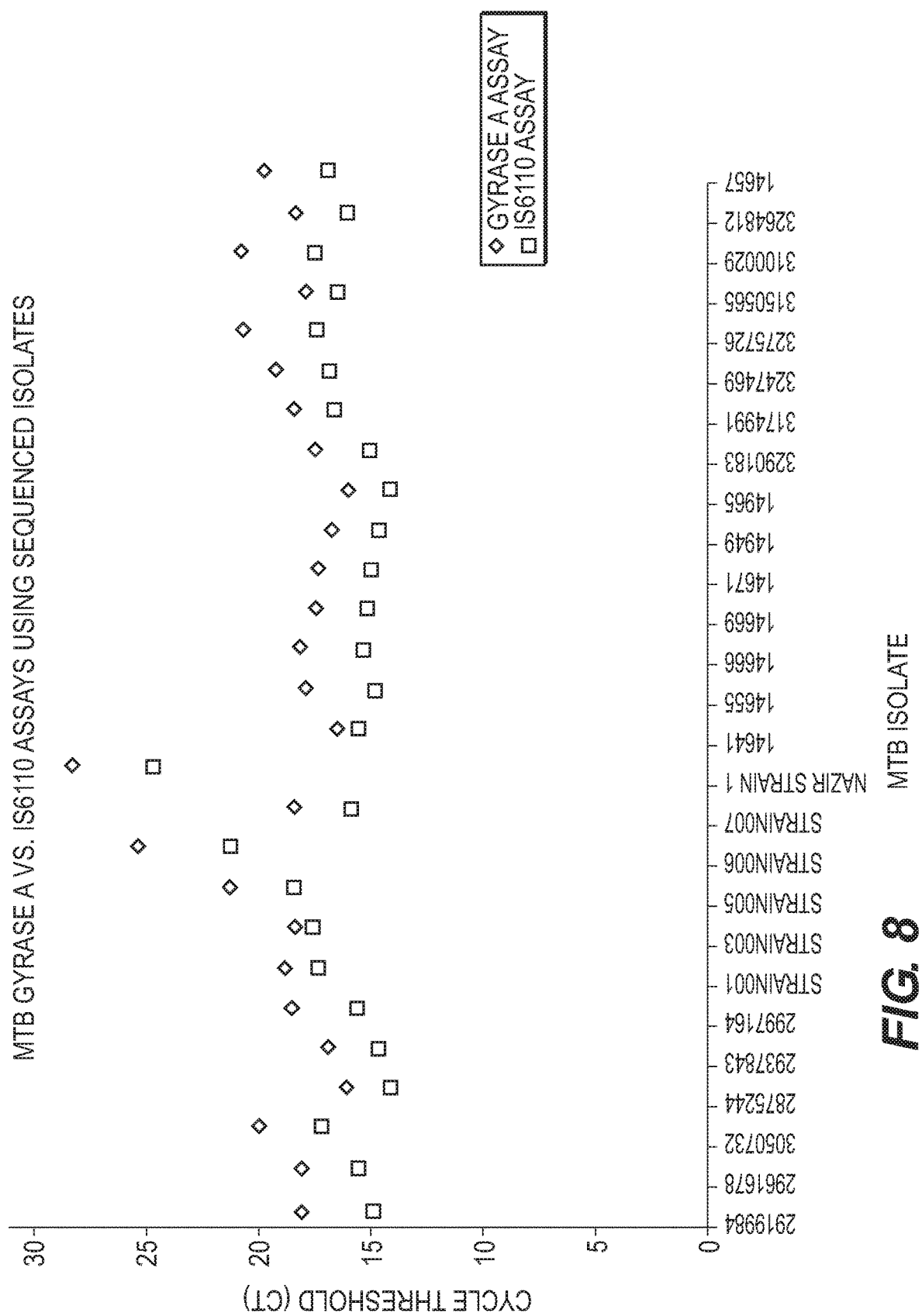

Gyrase PCR for the Detection of TB vs. 6110 PCR assay. The gyrase target for OCR and whole Gyrase gene sequencing on the Ion Torrent PGM can also be used to identify TB mutations that lead to resistance. This second PCR target allows for the accurate analysis of TB strains that may not include the entire IS6110 insertion element. While the IS6110 assay has multiple gene copies in most strains, some have only one. As shown in FIGS. 6, 7 and 8, this Gyrase assay has a generally higher cycle threshold in comparison to the IS6110 assay due to multiple IS6110 gene copies in those isolates and thus more sensitivity. Thus any possible TB mutation can be followed—even away from the detection site by this method of full gene sequencing.

Phenotypic and genotypic results. Amino Acid characterization of 26 M. tuberculosis isolates by Ion Torrent sequencing of rpoB, katG, pncA, gyrA, and rrs (16s) genes are summarized in Tables 1-5, respectively, and compared to BACTEC™ MGIT™ 960 (phenotypic), and/or HAIN GenoType® MTBDRplus (genotypic) LPA. Of the 26 MTB clinical isolates, 14 (54%) were MDR, 7 (27%) were XDR, and 5 (19%) were sensitive to drugs by BACTEC™ MGIT™ 960 phenotypic analysis. The Ion Torrent PGM sequencing method showed 100% (26/26) concordance to both phenotypic resistance obtained by MGIT™ 960 culture (Tables 1-5) and genotypic rpoB and katG data obtained by Hain LPA (Table 1, 2).

rpoB gene mutations. A total of 10 rpoB amino acid substitutions were identified in the 26 clinical isolates compared to the H37Rv wild type strain. The common S531L mutation was the most prevalent, but mutations in codons 516 and 526, also known to confer resistance to rifampin were observed (Table 1). Additionally, mutations were observed within the rpoB open reading frame but outside of the 81-basepair rifampin resistance-determining region (RRDR; Table 1). The V1941 mutation observed outside of the RRDR in one strain is a unique substitution that is likely not associated with rifampin resistance. Five amino acid substitutions were noted in at least one strain beyond residue position 900 of the rpoB protein. There were seven strains with an rpoB mutation (6 at position 516 and 1 at position 526) where a wild type band was absent without a corresponding mutation band according to LPA. In six of these seven isolates, Ion Torrent sequencing revealed an uncommon amino acid substitution (i.e., glycine) within a known mutation site at position 516 where a valine (V) substitution (D516V) is typically known to occur (Table 2). Similarly, in one isolate Ion Torrent sequencing revealed an arginine (R) within a known mutation site at position 526 where tyrosine (Y) or aspartic acid (D) substitutions (H526Y/D) typically occur.

katG gene mutations. Four amino acid substitutions were observed in the katG gene with S315T which is known to confer isoniazid resistance present in all resistant strains (Table 2). Clinical strains harboring R463L, W191R, and N138H mutations were detected by DST (Table 2) and have been previously characterized. A substitution at position 463 (R463L) in katG has been previously shown to have no effect on antibiotic resistance and can be used to categorize *M. tuberculosis* isolates into genetic Groups 1 (Arg463) or 2/3 (Leu463). Of 26 clinical isolates assessed, 7 (27%) were members of genetic Group 1 as evident by this R463L substitution.

pncA gene mutations. Seven nucleotide mutations were noted in at least one strain among 561 bps comprising the full-length coding region for the pncA gene (Table 3). Nine of 26 strains (34.6%) contained an amino acid mutation conferring pyrazinamide resistance (Table 3). In one strain, a silent (synonymous) nucleotide mutation was characterized at nucleotide position 195 (C195T). Five strains contained previously characterized amino acid substitutions (C14R, A102V, V139G, R154G, and L172P) known to confer resistance to pyrazinamide. A novel mutation, not previously reported elsewhere, encoding a termination stop codon was found in one isolate at residue 122 (Q122Stop) in the pncA protein (Table 3).

gyrA gene mutations. Nine unique mutations were observed in the 2,517 bp full-length gyrA gene encoding subunit A of the DNA gyrase enzyme. Resistance to fluoroquinolones (FQ) was only noted in strains harboring mutations in the quinolone resistance determining region (QRDR) defined by substitutions in gyrA at codons 88, 90, and 94. A number of additional mutations were also observed in regions outside of the QRDR including two 'mixed strain' mutations at position 549 and 613 in the gyrA protein (Table 4). Mutation at position 95 (S95T) is known to have no effect on FQ resistance but can be used to categorize strains in genetic Groups 2 or 3. Of the 19 total clinical isolates belonging to genetic Groups 2/3, 18 (96%) were Group 2, and 1 (4%) was Group 3 according to assessment of gyrA position 95 (T=genetic Group 2, and S=genetic Group 3).

rrs (16s) gene mutations. Four nucleotide mutations were noted among the 1,540 bps comprising the full length 16s rrs gene. Seven of 26 (27%) clinical isolates were shown to be resistant to aminoglycosides by DST, and all strains harbored an A1401G mutation known to confer resistance (Table 5). Two other amino acid mutations (C492T and A514C) were observed, but have been previously shown to not inhibit aminoglycoside efficacy. A previously uncharacterized G878A nucleotide mutation was observed, but the isolate was shown to be sensitive according to DST (Table 5).

Figure 9:
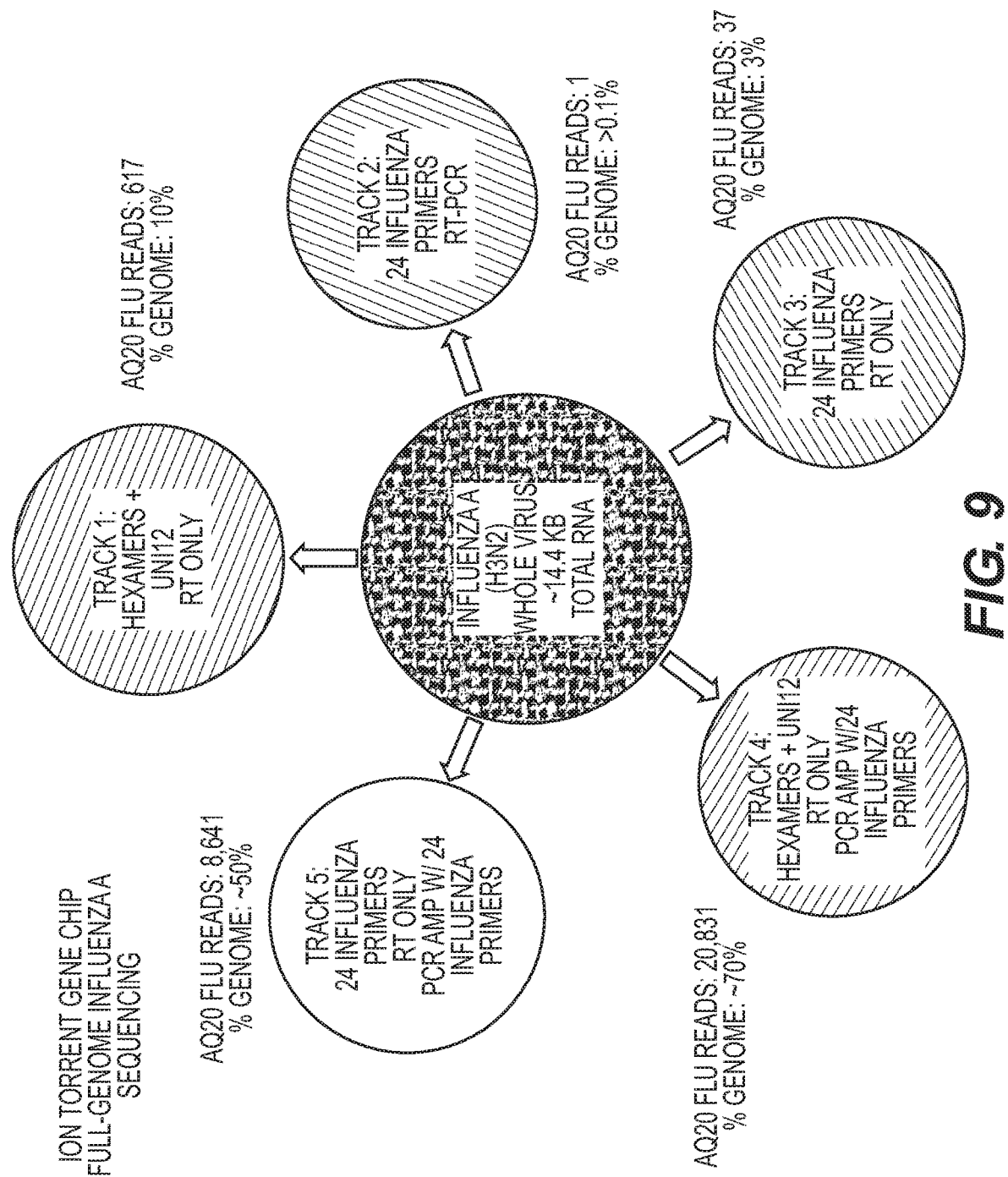
Figure 12:
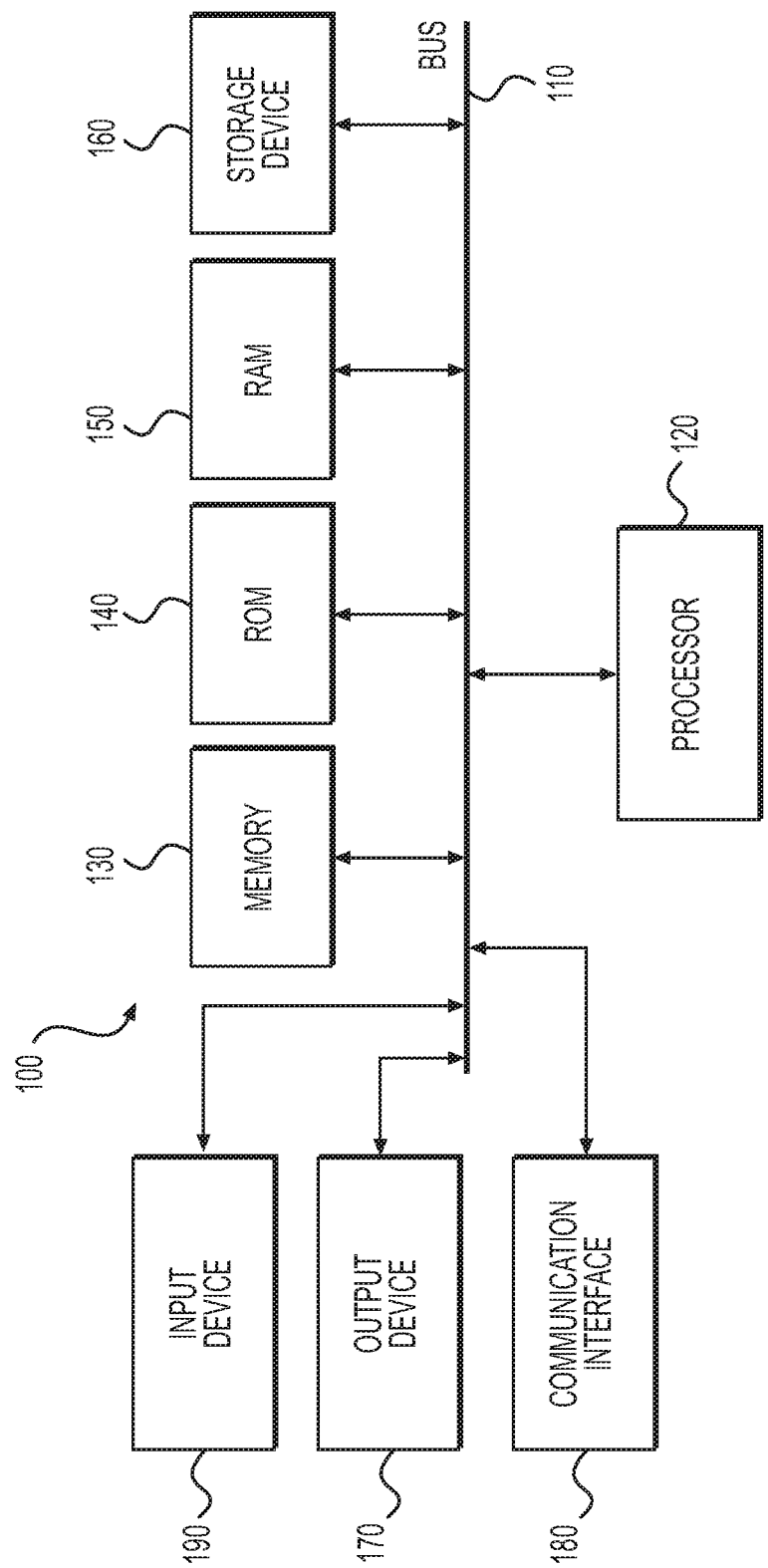

Megabase Sequencing. Ion torrent gene chip sequencing was performed on the complete genome of Influenza virus A under five distinct conditions, identified in FIG. 9 as Tracks. Whole viral nucleic acid of Influenza A, strain H3N2 (about 14.4 kb total RNA) was prepared as discussed above and either reverse transcribed only, or reverse transcribed and PCR amplified as indicated in FIG. 9. Influenza virus genome was mass amplified by reverse transcription (RT) and certain amplified cDNA populations subjected to PCR. Each result was then analyzed using the Ion Torrent sequencing protocol. RT and/or RT-PCR analysis was performed with uniform hexamers, Uni 12, and/or 24 different influenza-specific primers (different in both length and sequence). Uniform hexamers comprise a collection of primers, each six nucleotides in length whereby the collections contain all of sequence iterations of the six nucleotides. Uni 12 is primer that contains a sequence that is complimentary to 12 nucleotides at the 3' terminus of each of the segments of the influenza H3N2 viral genome (5'-ACGCGTGATCAGCAAAAGCAGG; SEQ ID NO 13). As shown in FIG. 9, Track 4 amplification and sequencing with hexamer primers and Uni 12 followed by PCR amplification with the 24 influenza-specific primers and Ion Torrent protocol sequencing identified about 70% of the influenza genome.

Additional experiments were performed to achieve one-step sequencing of the complete Influenza genome. A series of influenza-specific primers were developed that would allow for uniform conditions to be performed for a PCR reaction. The primers that were developed are listed in FIG. 10. These primers are all specific for the influenza virus genome with primer pairs spaced along the genome about every 800 to 1,000 bases in length (see FIG. 10, amplicon length and start and stop positions for primer placement and sequence). All primers were of similar length, about 18-23 nucleotides and contain a similar GC content, about 22.7% to 38.9%, with nearly about 33%±6% and most about 33%±3%. PCR analysis was performed using different collections of these primers and the amplified products identified using the Ion Torrent sequencing protocol.

Figure 11B:
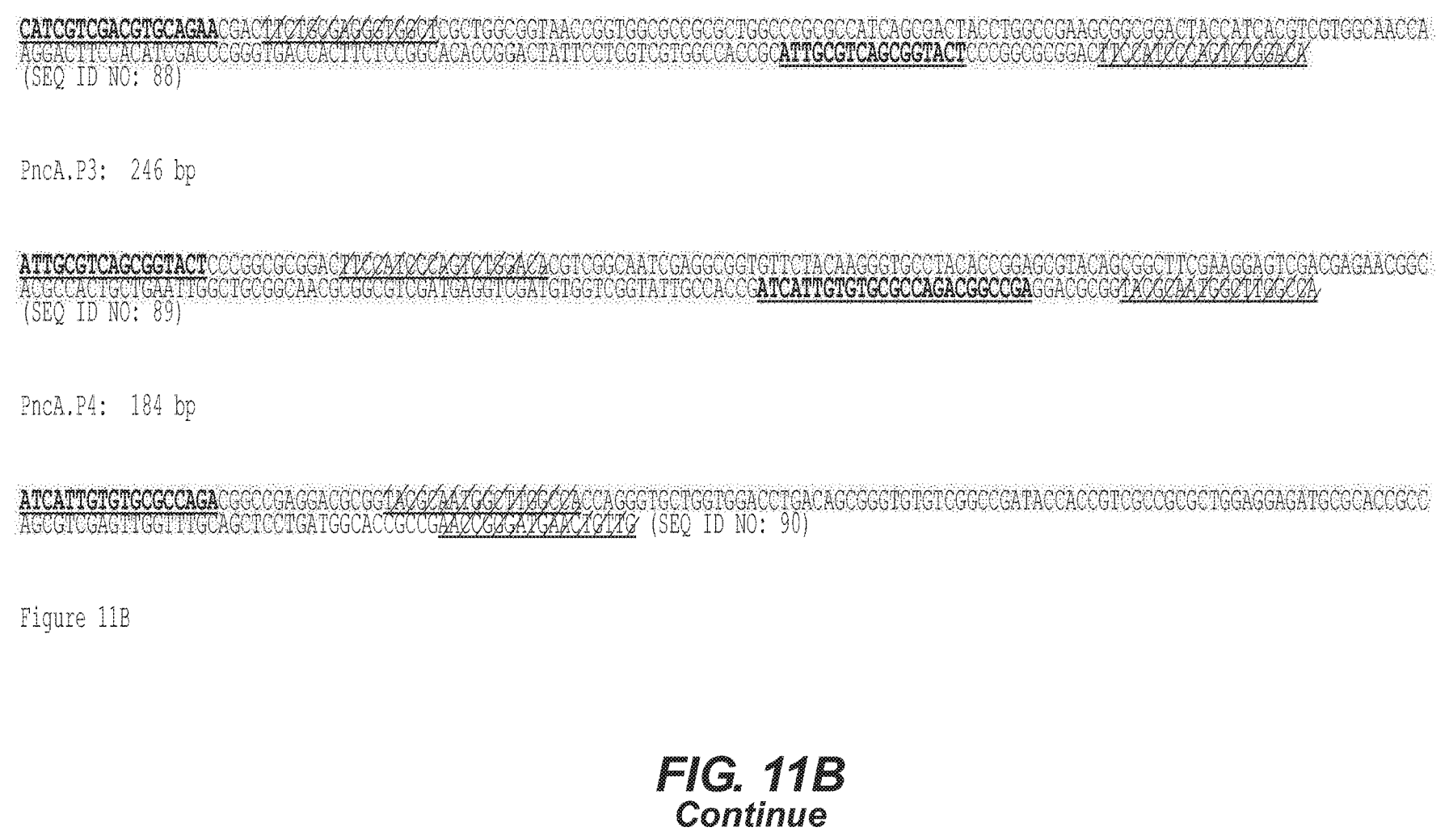

Sequencing of pncA gene. The gene sequence of pncA for PZA resistance was determined using a series of primers spaced or "tiled" along the pncA gene in accordance with the invention and compared to results achieved with traditional Sanger sequencing. The coding sequence of the pncA gene is depicted in FIG. 11A and the primers utilized are depicted in FIG. 11B in bold and underlined. Using these primers in conjunction with Ion Torrent methodology, the entire coding regions of pncA was determined (see P1-P4 of FIG. 11B). Expanding the primers utilized to all genes or of specific regions allows for one-step sequencing of the entire genome. The surprising results achieved identified 2 or 11 cases of mixed strain (heterogenous) populations that contain both wild-type and mutant that would have been missed by traditional Sanger sequencing. A summary of the amino acid mutations in pncA of MTB clinical isolates deduced by Ion Torrent according to the methods of the invention is shown in Table 7 and can be compared with Table 8 showing the results achieved with Sanger sequencing.

TABLE 7

| Sample No. | pncA Mutation (561 bp)** | Phenotype |
|---|---|---|
| NT3346 | INDEL deletion of T at pos 12 causes stop at pos 4 | Resistant |
| NT661/1 | Missense INDEL deletion of T at pos 582 | Resistant |
| ML1632/2 | promoter, insert T after C at pos 12 | Resistant |
| Sz-426/12 | wildtype | Sensitive |
| FS4751103/1 | Missense INDEL G inserted at pos 35 | Resistant |
| W3797/2 | D12G* | Resistant |
| S2744 | H51D | Resistant |
| ML1440/2 | S59P* | Resistant |
| EC2248/1 | A79V* INDEL at Stop 127, insert at pos 360 in 82% of strains | Resistant |
| ML2482/1 | K96STOP* | Resistant |
| WC2601/2 | T135P* (seen in 61%) and silent T to C at pos 475 in 25% | Resistant |

*= There is a known heterogenous nucleotide mutation that confers mixed amino acid substitution
**= In comparison to H37Rv reference strain

TABLE 8

| Sample No. | pncA Mutation (561 bp)** | Phenotype |
|---|---|---|
| NT3346 | Insertion 12, STOP55 | Resistant |
| NT661/1 | Missense INDEL deletion of T at pos 582 | Resistant |
| ML1632/2 | promoter, insert T after C at pos 12 | Resistant |
| Sz-426/12 | ??? | ??? |
| FS4751103/1 | Missense INDEL G inserted at pos 35 | Resistant |
| W3797/2 | D12G* | Resistant |
| S2744 | ??? | Resistant |
| ML1440/2 | Wildtype | Resistant |
| EC2248/1 | A79V and Stop 126 | Resistant |
| ML2482/1 | K96STOP | Resistant |
| WC2601/2 | wildtype | Resistant |

**= In comparison to H37Rv reference strain

As shown in the comparison of Table 7 with Table 8, WC2601/2 showed a T135 mutation had no corresponding mutation by Sanger sequencing. The mutation was heterogeneous with 61% of cells containing the mutation with 29% as wildtype. With ML1440/2, a S59P mutation was identified with no corresponding mutation by Sanger sequencing. The mutation was heterogeneous with 95% containing the mutation with 5% wild-type.

Rapid characterization of drug resistance genes directly from patient sputum samples. The methods of the invention address a need for performing rapid characterization of drug resistance genes from patient sputum samples obtained from, for example, remote areas. The method includes collection to analysis of MTB rpoB and pncA genes that confer resistance to first line drugs, rifampicin and pyrazinamide, respectively. The methodology employs ambient temperature shipment of sputum in PrimeStore Molecular Transport Medium (MTM), nucleic acid extraction, gene amplification and sequencing directly from sputum for MTB drug resistance characterization.

Sputum specimens were collected as part of a large prospective analysis of MTB diagnosis in rural South Africa (patients in Mopani, South Africa). For molecular testing, a flocked swab (Copan Diagnostics, Brescia, Italy) was submerged and swirled a minimum of five times in sputum and then subsequently transferred into 1.5 mL of molecular transport medium, PrimeStore MTM® (PS-MTM). PS-MTM is a clinical transport solution that inactivates microbes including M. tuberculosis, and preserves and stabilizes released RNA/DNA for safe, ambient temperature shipment. PS-MTM tubes containing sputum were all shipped from South Africa to a fully equipped facility in San Antonio, Tex. at ambient temperature using a commercial carrier.

Total genomic DNA was purified using the PrimeXtract kit (Longhorn Vaccines and Diagnostics, San Antonio, Tex., USA) according to manufacturer's recommendations. Real-time PCR amplification of MTB was performed using PrimeMix TB® (PM-PCR), an all-inclusive reagent blend that targets the highly conserved MTB IS6110 region.

PCR amplification using MTB primers for pncA and rpoB were performed as previously described. Primers for rpoB (1,625 bps) and pncA (960 bps) amplify a portion of the gene containing the full rpoB determining region and the promoter plus full coding region of the pncA gene, respectively. For NGS library preparation, pncA and rpoB gene amplicons were prepared using the Nextera XT Sample Prep Kit. MiSeq NGS was performed according to manufacturer's instructions (Illumina, San Diego, Calif., USA) using MiSeq Reagent Kit (V3) with 600 cycles. Bioinformatics were performed using SeqMan NGen (V8) and LaserGene (V12) Core Suite (DNAStar, Inc, USA) with genetic comparison to the H37Rv reference strain.

Of the 22 specimens selected for rpoB and pncA NGS, 17 (77.3%) produced complete DNA sequence (Table 9). A total of five samples were omitted due to partial gene sequencing, poor sequence quality, or low coverage depth (i.e., below 10×). Specimens producing full sequence had PCR real-time values ranging from 23.5 to 37.4, with the majority having CT values less than 30. Success in obtaining quality NGS from original specimens hinges on the concentration of MTB recovered during extraction. Using a qualitative real-time PCR assay prior performing endpoint amplification of MTB resistance genes may be predictive of NGS success. In three specimens NGS do not produce suitable data, most likely due to inefficient amplification in the longer 1625 bp rpoB PCR amplicon (Table 9).

TABLE 9

Ion Torrent Sequencing* of MTB rpoB and pncA gene from selected patient sputum testing positive by Primemix MTB real-time PCR (N-22)

| Patient | Primemix RT-PCR | Xpert/RIF | MGIT | ion torrent seq'ing mutations rpoB | pncA |
|---|---|---|---|---|---|
| 104 | + (CT = 23.5) | + | + | wt | wt |
| 64 | + (CT = 25.2) | + | + | wt | wt |
| 117 | + (CT = 25.4) | +/RIF** res | + | H-526-D# | wt |
| 54 | + (CT = 26.0) | + | − | C-309-T# | wt |
| 47 | + (CT = 26.7) | + | + | wt | wt |
| 119 | + (CT = 27.2) | + | + | wt | wt |
| 83 | + (CT = 28.3) | + | + | wt | wt |
| 74 | + (CT = 28.8) | + | + | wt | wt |
| 71 | + (CT = 28.9) | +/RIF** res | + | H-526-Y# | wt |
| 89 | + (CT = 28.9) | + | + | V-194-I# | wt |
| 81 | + (CT = 29.5) | + | + | wt | wt |
| 50 | + (CT = 30.7) | +/RIF** res | + | H-526-Y# | wt |
| 85 | + (CT = 33.8) | + | C | NA | NA |
| 72 | + (CT = 34) | + | − | NA | wt |
| 134 | + (CT = 34.4) | + | + | NA | NA |
| 2 | + (CT = 35.2) | + | − | NA | wt |
| 127 | + (CT = 36.0) | + | + | NA | NA |
| 20 | + (CT = 36.0) | + | C | wt | wt |
| 10 | + (CT = 37.4) | + | − | wt | wt |
| 110 | + (CT = 38.0) | + | − | NA | NA |
| 108 | + (CT = 38.7) | + | − | NA | R-2-P## |
| 120 | + (CT = 39.4) | + | − | NA | NA |

*= Illumina MiSeq to amplify the full 561 base pair pncA gene plus 45 base pairs promotor region (606 base pairs) and a 1608 bp rpoB gene region that included the rpoB determining region.
**RIF = rifampin resistant.
wt = wild-type according to H37Rv strain.
NA = sequence no available
mutation at position 526 of the rpoB gene is known for resistance mutation.
mutation at position 2 of the pncA gene (arginine-2-proline).

Resistance mutations were found in rpoB gene sequences which correlated with those determined by Xpert. Upon rpoB gene NGS characterization, three specimens contained classical resistance mutations at position 526 of the rpoB determining region. Interestingly, two specimens contained a H-526-Y and one a H-526-D mutation (Table 9). A V-194-I substitution was observed in one specimen (Patient 89) that has been shown previously to be a non-resistance conferring mutation. A synonymous silent mutation, i.e., C-309-T was noted in the rpoB of one specimen. The pncA gene sequences from all strains were found to be wild type in comparison to the H37RV reference strain (Table 9), with the exception of a novel R-2-P mutation in one specimen. It is not known whether this mutation confers resistance to pyrazinamide, and since it was not detected by Xpert or MGIT culture no drug resistance data is available for this specimen. The patient from whom this specimen was derived presented with persistent cough and weight loss. Follow up testing of this patient using real-time PCR was low positive (CT=36.1) but Xpert and MGIT culture were negative.

The ability to improve MTB detection with sensitive real-time PCR and then rapidly sequence resistance genes provides another opportunity for low resource areas. Since PS-MTM rapidly kills MTB and preserves the DNA at ambient temperature and above, specimens can be efficiently transported for real-time PCR and sequencing to improve detection of drug resistant strains and optimize patient therapy. Previous studies have shown the benefit of sequencing MDR strains from patients who have come to the US from countries with MDR and XDR to identify known and new resistance mutations. An additional advantage of NGS is that the depth of coverage provides the ability to detect more than one population, i.e., heteroresistance in the patient's specimen. Heteroresistant characterization is important for patient care, especially if MTB subpopulations that are resistant to key antibiotics as these become the predominant patient strain. This example also demonstrates the feasibility of transporting sputum specimens efficiently to central and regional labs to provide support to rural clinics. Without adding extra training staff or infrastructure, patient sputum specimens from rural areas can be transported to labs with highly trained personnel and state of the art equipment to support MTB patient care surveillance and research.

Characterization of *Mycobacterium tuberculosis* (MTB) drug resistance genes is critical for the appropriate treatment of *tuberculosis* (TB). Molecular detection and next-generation sequencing (NGS) are rapidly providing new tools to diagnose and improve treatment of drug resistant TB. Understanding the epidemiology and the role of mobile populations in rapidly changing resistance patterns, particularly in rural African settings is important as we work to treat and eradicate TB. In this brief report, NGS was used to characterize MTB rpoB and pncA drug resistance genes directly from sputum collected and transported at ambient temperature from rural South Africa to Tex. in PrimeStore® MTM (PS-MTM). These genes confer resistance to first line drugs, rifampicin and pyrazinamide, respectively. This work is significant because stable specimens containing high quality DNA enable rapid, centralized processing directly from sputum.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A mixture comprising multiple pairs of nucleic acid primers wherein,
   each primer is from about 15 to about 25 nucleotides in length;
   each primer has a GC content of from about 25% to about 45%;
   the multiple pairs of nucleic acid primers contain sequences that correspond to different portions of the genome of a Mycobacteria, wherein the multiple pairs contain nucleic acid primers that hybridize with portions of sequences of genes that confer resistance to the Mycobacteria of multiple agents selected from the group consisting of rifampin, isoniazid, fluoroquinolone, pyrazinamide, aminoglycoside, amikacin, kanamycin, capreomycin and streptomycin; and
   the different portions are spaced about 500 to about 2,000 nucleotides apart along the entire sequence of the genome.

2. The mixture of claim 1, wherein each primer of the multiple pairs of nucleic acid primers has a similar annealing temperature to the nucleic acid.

3. The mixture of claim 2, wherein the similar annealing temperature is within about 5° C.

4. The mixture of claim 2, wherein the similar annealing temperature is within about 3° C.

5. The mixture of claim 1, wherein the different portions are spaced about 800 to about 1,500 nucleotides apart.

6. The mixture of claim 1, which is maintained at room temperature and does not require refrigeration.

7. The mixture of claim 1, wherein the Mycobacteria is *Mycobacterium tuberculosis*.

8. The mixture of claim 1, wherein the nucleic acid primers do not self-hybridize.

9. The mixture of claim 1, further containing a heat-stable polymerase, a mix of deoxynucleotide tri phosphates comprising dATP, dCTP, dGTP and dTTP, a chelating agent, a salt, a buffer, a stabilizing agent, and/or nuclease-free water.

10. The mixture of claim 1, further containing a reverse transcriptase, a mix of deoxynucleotide tri phosphates comprising about equivalent amounts of dATP, dCTP, dGTP and dTTP, a chelating agent, an osmolarity agent, an albumin, a magnesium salt, and/or a buffer.

11. The mixture of claim 1, which, when the mixture and the genome are subjected to a polymerase chain reaction, generates a collection of amplicons, such that the entire sequence of the genome is represented in the resulting collection of amplicons.

12. The mixture of claim 11, wherein the collection comprises amplicons that are from about 500 to 2,000 nucleotides.

13. The mixture of claim 1, wherein each of the primers of the multiple primer pairs is from about 16 to about 24 nucleotides in length.

14. The mixture of claim 1, wherein each of the primers of the multiple primer pairs has a GC content of about 28% to about 35%.

15. The mixture of claim 1, wherein the multiple pairs of nucleic acid primers contain sequences that correspond to different portions of genes that confer resistance to at least three of the multiple agents.

16. The mixture of claim 1, wherein the multiple pairs of nucleic acid primers contain sequences that correspond to different portions of genes that confer resistance to at least five of the multiple agents.

17. The mixture of claim 1, wherein the multiple pairs of nucleic acid primers contain sequences that correspond to different portions of genes that confer resistance to at least seven of the multiple agents.

18. The mixture of claim 1, wherein the multiple pairs of nucleic acid primers contain sequences that correspond to different portions of genes that confer resistance to all of the multiple agents.

19. The mixture of claim 11, where the collection of amplicons includes one or more amplicons of sequences of genes that confer resistance to the Mycobacteria of multiple agents selected from the group consisting of rifampin, isoniazid, fluoroquinolone, pyrazinamide, aminoglycoside, amikacin, kanamycin, capreomycin and streptomycin.

20. A mixture comprising multiple pairs of nucleic acid primers wherein,
   the multiple pairs of nucleic acid primers contain sequences that correspond to different portions of the genome of a Mycobacteria, wherein the multiple pairs contain nucleic acid primers that hybridize with portions of sequences of genes that confer resistance to the Mycobacteria of multiple agents selected from the group consisting of rifampin, isoniazid, fluoroquinolone, pyrazinamide, aminoglycoside, amikacin, kanamycin, capreomycin and streptomycin;
   wherein, when the mixture and the genome are subjected to a polymerase chain reaction, generates a collection of amplicons that includes one or more amplicons of sequences of genes that confer resistance to the Mycobacteria of multiple agents selected from the group consisting of rifampin, isoniazid, fluoroquinolone, pyrazinamide, aminoglycoside, amikacin, kanamycin, capreomycin and streptomycin.

21. The mixture of claim 20, wherein each primer is from about 15 to about 25 nucleotides in length; each primer has a GC content of from about 25% to about 45%, each primer has a similar annealing temperature, and/or the different portions are spaced about 500 to about 2,000 nucleotides apart along the entire sequence of the genome.

22. The mixture of claim 20, wherein the multiple pairs of nucleic acid primers contain sequences that correspond to different portions of genes that confer resistance to at least three of the multiple agents.

23. The mixture of claim 20, wherein the multiple pairs of nucleic acid primers contain sequences that correspond to different portions of genes that confer resistance to at least five of the multiple agents.

24. The mixture of claim 20, wherein the multiple pairs of nucleic acid primers contain sequences that correspond to different portions of genes that confer resistance to at least seven of the multiple agents.

25. The mixture of claim 20, wherein the multiple pairs of nucleic acid primers contain sequences that correspond to different portions of genes that confer resistance to all of the multiple agents.

* * * * *